United States Patent
Gitchell et al.

(10) Patent No.: US 12,165,763 B2
(45) Date of Patent: *Dec. 10, 2024

(54) MEDICATION TRACKING

(71) Applicant: Bluesight, Inc., Alexandria, VA (US)

(72) Inventors: Jennifer Ashley Gitchell, Washington, DC (US); Timothy James Leo Kress-Spatz, Arlington, VA (US); Kevin William MacDonald, Miami, FL (US); Nicholas Bastien Petersen, Washington, DC (US); Julie Christina Meloni, Washington, DC (US); Christian Lee Doyle, Silver Spring, MD (US); Michael David Waud, Washington, DC (US); David Mario Pedra, Washington, DC (US); Nicholas Ward Stocchero, Washington, DC (US); Michael Christopher Wimpee, Washington, DC (US); Steven Shyu, Washington, DC (US); Mahesh Murali, Washington, DC (US)

(73) Assignee: Bluesight, Inc., Alexandria, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/154,646

(22) Filed: Jan. 13, 2023

(65) Prior Publication Data
US 2023/0377728 A1    Nov. 23, 2023

Related U.S. Application Data

(63) Continuation of application No. 17/177,914, filed on Feb. 17, 2021, now Pat. No. 11,557,393, which is a (Continued)

(51) Int. Cl.
*G16H 40/20* (2018.01)
*A61J 1/00* (2023.01)
(Continued)

(52) U.S. Cl.
CPC ............... *G16H 40/20* (2018.01); *A61J 1/00* (2013.01); *A61J 1/18* (2013.01); *G06K 7/10366* (2013.01);
(Continued)

(58) Field of Classification Search
CPC .... G16H 40/20; A61J 1/00; A61J 1/18; G06Q 10/087
(Continued)

(56) References Cited

U.S. PATENT DOCUMENTS

| | | |
|---|---|---|
| 4,884,827 A | 12/1989 | Kelley |
| 4,961,533 A | 10/1990 | Teller et al. |

(Continued)

FOREIGN PATENT DOCUMENTS

| | | |
|---|---|---|
| CA | 2 722 328 | 10/2009 |
| CA | 2 790 220 | 6/2013 |

(Continued)

OTHER PUBLICATIONS

"AmerisourceBergen Specialty Group Reconfigures Cubixx Medical Cabinet", Jan. 9, 2011, pp. 2, <https://web.archive.org/web/20180620192642/http://pharmaceuticalcommerce.com/supply-chain- logistics/amerisourcebergen-specialty-group-reconfigures-cubixx-medical-cabinet/>.

(Continued)

*Primary Examiner* — Ahshik Kim
(74) *Attorney, Agent, or Firm* — Knobbe, Martens, Olson & Bear, LLP

(57) ABSTRACT

A system and method is described for printing a label with an RFID tag. The system includes an RFID reader that queries a first RFID tag coupled to a first medicinal container that includes a medication. In response, the system receives a first unique identifier and uses the first unique identifier to determine a status of the medication, associate the first (Continued)

medicinal container with a medical provider and print a second label that includes a second RFID tag for a second medicinal container.

20 Claims, 14 Drawing Sheets

Related U.S. Application Data continuation of application No. 16/822,459, filed on Mar. 18, 2020, now Pat. No. 10,930,393, which is a continuation of application No. 16/103,001, filed on Aug. 14, 2018, now Pat. No. 10,600,513, which is a continuation of application No. 15/426,302, filed on Feb. 7, 2017, now Pat. No. 10,083,766, which is a continuation of application No. 14/876,533, filed on Oct. 6, 2015, now Pat. No. 9,582,644, which is a continuation of application No. 14/563,732, filed on Dec. 8, 2014, now Pat. No. 9,171,280.

(60) Provisional application No. 62/062,845, filed on Oct. 11, 2014, provisional application No. 62/020,576, filed on Jul. 3, 2014, provisional application No. 62/000,570, filed on May 20, 2014, provisional application No. 61/913,337, filed on Dec. 8, 2013.

(51) Int. Cl.
| | | |
|---|---|---|
| *A61J 1/18* | (2023.01) | |
| *G06K 7/10* | (2006.01) | |
| *G06Q 10/087* | (2023.01) | |
| *G06Q 50/22* | (2018.01) | |
| *G16Z 99/00* | (2019.01) | |
| *A61G 12/00* | (2006.01) | |

(52) U.S. Cl.
CPC .......... *G06Q 10/087* (2013.01); *G06Q 50/22* (2013.01); *G16Z 99/00* (2019.02); *A61G 12/001* (2013.01); *A61J 2205/30* (2013.01); *A61J 2205/60* (2013.01)

(58) Field of Classification Search
USPC ......................................................... 235/375
See application file for complete search history.

(56) References Cited

U.S. PATENT DOCUMENTS

| | | |
|---|---|---|
| 5,713,485 A | 2/1998 | Liff et al. |
| 5,930,145 A | 7/1999 | Yuyama et al. |
| 5,963,134 A | 10/1999 | Bowers et al. |
| 5,986,662 A | 11/1999 | Argiro et al. |
| 6,112,502 A | 9/2000 | Frederick et al. |
| 6,249,299 B1 | 6/2001 | Tainer |
| 6,275,157 B1 | 8/2001 | Mays et al. |
| 6,294,999 B1 | 9/2001 | Yarin et al. |
| 6,330,351 B1 | 12/2001 | Yasunaga |
| 6,574,166 B2 | 6/2003 | Niemiec |
| 6,632,619 B1 | 10/2003 | Harrison et al. |
| 6,771,369 B2 | 8/2004 | Rzasa et al. |
| 6,825,864 B2 | 11/2004 | Botten et al. |
| 6,847,861 B2 | 1/2005 | Lunak et al. |
| 6,851,615 B2 | 2/2005 | Jones |
| 6,861,954 B2 | 3/2005 | Levin |
| 6,877,658 B2 | 4/2005 | Raistrick et al. |
| 6,879,876 B2 | 4/2005 | O'Dougherty et al. |
| 6,900,021 B1 | 5/2005 | Harrison et al. |
| 6,933,849 B2 | 8/2005 | Sawyer |
| 6,935,560 B2 | 8/2005 | Andreasson et al. |
| 6,952,681 B2 | 10/2005 | McQuade et al. |
| 6,985,870 B2 | 1/2006 | Martucci et al. |
| 6,992,574 B2 | 1/2006 | Aupperle et al. |
| 6,994,249 B2 | 2/2006 | Peterka et al. |
| 7,036,729 B2 | 5/2006 | Chung |
| 7,061,831 B2 | 6/2006 | De La Huerga |
| 7,111,780 B2 | 9/2006 | Broussard et al. |
| 7,116,343 B2 | 10/2006 | Botten et al. |
| 7,118,029 B2 | 10/2006 | Nycz et al. |
| 7,140,542 B2 | 11/2006 | Andreasson et al. |
| 7,146,247 B2 | 12/2006 | Kirsch et al. |
| 7,151,456 B2 | 12/2006 | Godfrey |
| 7,158,030 B2 | 1/2007 | Chung |
| 7,165,077 B2 | 1/2007 | Kalies |
| 7,175,081 B2 | 2/2007 | Andreasson et al. |
| 7,177,721 B2 | 2/2007 | Kirsch et al. |
| 7,178,729 B2 | 2/2007 | Shaffer et al. |
| 7,182,256 B2 | 2/2007 | Andreasson et al. |
| 7,212,100 B2 | 5/2007 | Terenna |
| 7,212,127 B2 | 5/2007 | Jacober et al. |
| 7,227,469 B2 | 6/2007 | Varner et al. |
| 7,232,066 B2 | 6/2007 | Andreasson et al. |
| 7,253,736 B2 | 8/2007 | Tethrake et al. |
| 7,256,699 B2 | 8/2007 | Tethrake et al. |
| 7,263,501 B2 | 8/2007 | Tirinato et al. |
| 7,264,323 B2 | 9/2007 | Tainer et al. |
| 7,268,684 B2 | 9/2007 | Tethrake et al. |
| 7,275,645 B2 | 10/2007 | Mallett et al. |
| 7,299,981 B2 | 11/2007 | Hickle et al. |
| 7,316,231 B2 | 1/2008 | Hickle |
| 7,317,393 B2 | 1/2008 | Maloney |
| 7,318,529 B2 | 1/2008 | Mallett et al. |
| 7,339,550 B2 | 3/2008 | Hayama et al. |
| 7,341,147 B2 | 3/2008 | Mallett et al. |
| 7,348,884 B2 | 3/2008 | Higham |
| 7,354,884 B2 | 4/2008 | Hada et al. |
| 7,362,228 B2 | 4/2008 | Nycz et al. |
| 7,375,737 B2 | 5/2008 | Botten et al. |
| 7,394,383 B2 | 7/2008 | Hager et al. |
| 7,440,818 B2 | 10/2008 | Handfield et al. |
| 7,446,747 B2 | 11/2008 | Youngblood et al. |
| 7,454,880 B1 | 11/2008 | Austin et al. |
| 7,486,188 B2 | 2/2009 | Van Alstyne |
| 7,492,257 B2 | 2/2009 | Tethrake et al. |
| 7,492,261 B2 | 2/2009 | Cambre et al. |
| 7,504,954 B2 | 3/2009 | Spaeder |
| 7,518,502 B2 | 4/2009 | Austin et al. |
| 7,518,516 B2 | 4/2009 | Azevedo et al. |
| 7,551,089 B2 | 6/2009 | Sawyer |
| 7,559,483 B2 | 7/2009 | Hickle et al. |
| 7,564,364 B2 | 7/2009 | Zweig |
| 7,630,791 B2 | 12/2009 | Nguyen et al. |
| 7,639,136 B1 | 12/2009 | Wass et al. |
| 7,644,016 B2 | 1/2010 | Nycz et al. |
| 7,672,872 B2 | 3/2010 | Shanton |
| 7,706,915 B2 | 4/2010 | Mohapatra et al. |
| 7,706,916 B2 | 4/2010 | Hilton |
| 7,712,670 B2 | 5/2010 | Sauerwein, Jr. et al. |
| 7,715,277 B2 | 5/2010 | De La Huerga |
| 7,729,597 B2 | 6/2010 | Wright et al. |
| 7,734,157 B2 | 6/2010 | Wright et al. |
| 7,737,858 B2 | 6/2010 | Matityaho |
| 7,747,477 B1 | 6/2010 | Louie et al. |
| 7,752,085 B2 | 7/2010 | Monroe |
| 7,772,964 B2 | 8/2010 | Tethrake et al. |
| 7,775,056 B2 | 8/2010 | Lowenstein |
| 7,783,163 B2 | 8/2010 | Wright et al. |
| 7,783,174 B2 | 8/2010 | Wright et al. |
| 7,801,422 B2 | 9/2010 | Wright et al. |
| 7,815,117 B2 | 10/2010 | Tuschel et al. |
| 7,834,765 B2 | 11/2010 | Sawyer |
| 7,834,766 B2 | 11/2010 | Sawyer |
| 7,837,093 B1 | 11/2010 | Leu et al. |
| 7,837,107 B1 | 11/2010 | Leu et al. |
| 7,858,841 B2 | 12/2010 | Krautkramer et al. |
| 7,860,730 B1 | 12/2010 | Goodall et al. |
| 7,868,754 B2 | 1/2011 | Salvat, Jr. |
| 7,893,876 B2 | 2/2011 | Brown et al. |
| 7,908,030 B2 | 3/2011 | Handfield et al. |
| 7,918,830 B2 | 4/2011 | Langan et al. |
| 7,928,844 B2 | 4/2011 | Mackenzie et al. |
| 7,933,033 B2 | 4/2011 | Ohishi et al. |

(56) References Cited

U.S. PATENT DOCUMENTS

| | | |
|---|---|---|
| 7,976,508 B2 | 7/2011 | Hoag |
| 7,985,711 B2 | 7/2011 | Tohmatsu et al. |
| 7,990,272 B2 | 8/2011 | Wass et al. |
| 7,996,286 B2 | 8/2011 | Kreiner et al. |
| 8,002,174 B2 | 8/2011 | Coyne, III et al. |
| 8,006,903 B2 | 8/2011 | Braun et al. |
| 8,009,913 B2 | 8/2011 | Greyshock |
| 8,019,471 B2 | 9/2011 | Bogash et al. |
| 8,031,347 B2 | 10/2011 | Edwards et al. |
| 8,042,738 B2 | 10/2011 | Cloix |
| 8,049,627 B1 | 11/2011 | Addante |
| 8,063,925 B2 | 11/2011 | Tainer et al. |
| 8,065,858 B2 | 11/2011 | Leu et al. |
| 8,072,635 B2 | 12/2011 | Roberts et al. |
| 8,077,041 B2 | 12/2011 | Stern et al. |
| 8,082,192 B2 | 12/2011 | Nycz et al. |
| 8,099,339 B1 | 1/2012 | Pinsonneault et al. |
| 8,108,068 B1 | 1/2012 | Boucher et al. |
| 8,111,159 B2 | 2/2012 | Andreasson et al. |
| 8,112,175 B2 | 2/2012 | Handfield et al. |
| 8,131,397 B2 | 3/2012 | Vahlberg et al. |
| 8,154,390 B2 | 4/2012 | Heath et al. |
| 8,174,392 B1 | 5/2012 | Sagbhini et al. |
| 8,186,587 B2 | 5/2012 | Zmood et al. |
| 8,212,677 B2 | 7/2012 | Ferguson |
| 8,219,413 B2 | 7/2012 | Martinez et al. |
| 8,224,483 B1 | 7/2012 | Ansari et al. |
| 8,231,749 B2 | 7/2012 | Dent et al. |
| 8,258,961 B2 | 9/2012 | Phillips et al. |
| 8,261,939 B2 | 9/2012 | Knoth |
| 8,271,128 B1 | 9/2012 | Schultz |
| 8,279,069 B2 | 10/2012 | Sawyer |
| 8,283,287 B2 | 10/2012 | Aihara et al. |
| 8,284,059 B2 | 10/2012 | Ross |
| 8,285,083 B2 | 10/2012 | Canessa et al. |
| 8,285,607 B2 | 10/2012 | Danilewitz |
| 8,286,222 B2 | 10/2012 | Silverbrook et al. |
| 8,292,173 B2 | 10/2012 | Yturralde et al. |
| 8,292,186 B2 | 10/2012 | Deloche et al. |
| 8,296,950 B2 | 10/2012 | Colbrunn et al. |
| 8,313,024 B2 | 11/2012 | Marino |
| 8,319,607 B2 | 11/2012 | Grimlund et al. |
| 8,328,082 B1 | 12/2012 | Bochenko et al. |
| 8,339,649 B2 | 12/2012 | Ohishi et al. |
| 8,341,041 B2 | 12/2012 | Hull |
| 8,346,632 B2 | 1/2013 | Saghbini |
| 8,355,753 B2 | 1/2013 | Bochenko et al. |
| 8,355,962 B2 | 1/2013 | Delaney et al. |
| 8,359,338 B2 | 1/2013 | Butterfield et al. |
| 8,371,448 B1 | 2/2013 | Reaux |
| 8,376,228 B2 | 2/2013 | DeVet et al. |
| 8,384,545 B2 | 2/2013 | Hussain et al. |
| 8,385,972 B2 | 2/2013 | Bochenko et al. |
| 8,386,070 B2 | 2/2013 | Eliuk et al. |
| 8,394,053 B2 | 3/2013 | Bochenko et al. |
| 8,403,212 B2 | 3/2013 | van Esch |
| 8,403,224 B2 | 3/2013 | Fedorko et al. |
| 8,405,508 B2 | 3/2013 | Burke |
| 8,438,067 B2 | 5/2013 | Omura et al. |
| 8,461,076 B2 | 6/2013 | Okada et al. |
| 8,483,550 B2 | 7/2013 | Wright et al. |
| 8,509,604 B2 | 8/2013 | Wright et al. |
| 8,515,251 B2 | 8/2013 | Wright et al. |
| 8,519,849 B2 | 8/2013 | Ross-Messemer |
| 8,530,379 B2 | 9/2013 | Shimizu et al. |
| 8,564,416 B2 | 10/2013 | Steven et al. |
| 8,565,552 B2 | 10/2013 | Sommer et al. |
| 8,582,171 B2 | 11/2013 | Srnka et al. |
| 8,589,271 B2 | 11/2013 | Evans |
| 8,593,278 B2 | 11/2013 | Churbock et al. |
| 8,593,678 B2 | 11/2013 | Ohishi et al. |
| D694,817 S | 12/2013 | Adam et al. |
| 8,600,548 B2 | 12/2013 | Bossi et al. |
| 8,606,596 B1 | 12/2013 | Bochenko et al. |
| 8,636,202 B2 | 1/2014 | Keefe et al. |
| 8,639,525 B2 | 1/2014 | Levine et al. |
| 8,686,859 B2 | 4/2014 | Hussain et al. |
| 8,699,054 B2 | 4/2014 | Edwards et al. |
| 8,702,674 B2 | 4/2014 | Bochenko |
| 8,723,674 B2 | 5/2014 | Conley et al. |
| 8,749,356 B2 | 6/2014 | Hussain et al. |
| 8,755,056 B2 | 6/2014 | Edwards et al. |
| 8,825,680 B2 | 9/2014 | Burke et al. |
| 8,838,215 B2 | 9/2014 | John et al. |
| 8,868,616 B1 | 10/2014 | Otto et al. |
| 8,893,970 B2 | 11/2014 | Keefe et al. |
| 8,922,435 B2 | 12/2014 | Fontecchio et al. |
| 8,935,280 B2 | 1/2015 | Bauman et al. |
| 8,945,066 B2 | 2/2015 | Bochenko et al. |
| 8,948,478 B2 | 2/2015 | Keefe et al. |
| 8,985,388 B2 | 3/2015 | Ratnakar |
| 8,990,099 B2 | 3/2015 | MacDonald et al. |
| 9,037,479 B1 | 5/2015 | MacDonald et al. |
| 9,058,412 B2 | 6/2015 | MacDonald et al. |
| 9,058,413 B2 | 6/2015 | MacDonald et al. |
| 9,058,435 B2 | 6/2015 | Keefe et al. |
| 9,171,280 B2 * | 10/2015 | Gitchell ................. G06Q 50/22 |
| 9,189,769 B2 | 11/2015 | Caputo et al. |
| 9,367,665 B2 | 6/2016 | MacDonald et al. |
| 9,449,296 B2 | 9/2016 | MacDonald et al. |
| 9,539,374 B2 | 1/2017 | Halpern |
| 9,582,644 B2 | 2/2017 | Gitchell et al. |
| 9,734,294 B2 | 8/2017 | MacDonald et al. |
| 9,805,169 B2 | 10/2017 | MacDonald et al. |
| 10,083,766 B2 | 9/2018 | Gitchell et al. |
| 10,210,954 B2 | 2/2019 | Caputo et al. |
| 10,600,513 B2 | 3/2020 | Gitchell et al. |
| 10,609,845 B2 | 3/2020 | Elizondo, II |
| 10,621,394 B2 | 4/2020 | Hussain et al. |
| 10,643,743 B2 | 5/2020 | Caputo et al. |
| 10,658,077 B2 | 5/2020 | Hussain et al. |
| 10,658,078 B2 | 5/2020 | Caputo et al. |
| 10,664,740 B2 | 5/2020 | Elizondo, II |
| 10,853,380 B1 | 12/2020 | Agnew et al. |
| 10,930,393 B2 | 2/2021 | Gitchell et al. |
| 11,017,352 B2 | 5/2021 | MacDonald et al. |
| 11,037,342 B1 | 6/2021 | Agnew et al. |
| 11,139,075 B2 | 10/2021 | MacDonald et al. |
| 11,551,797 B2 | 1/2023 | Kress-Spatz et al. |
| 11,557,393 B2 | 1/2023 | Gitchell et al. |
| 11,664,105 B2 | 5/2023 | Yanowitz et al. |
| 2002/0026330 A1 | 2/2002 | Klein |
| 2002/0049650 A1 | 4/2002 | Reff |
| 2002/0087360 A1 | 7/2002 | Pettit |
| 2002/0087362 A1 | 7/2002 | Cobb et al. |
| 2002/0087554 A1 | 7/2002 | Seelinger |
| 2003/0055685 A1 | 3/2003 | Cobb et al. |
| 2003/0074223 A1 | 4/2003 | Hickle et al. |
| 2003/0102970 A1 | 6/2003 | Creel et al. |
| 2003/0160698 A1 | 8/2003 | Andreasson et al. |
| 2003/0216974 A1 | 11/2003 | Browne |
| 2004/0008123 A1 | 1/2004 | Carrender et al. |
| 2004/0032330 A1 | 2/2004 | Hoffman |
| 2004/0051368 A1 | 3/2004 | Caputo et al. |
| 2004/0057609 A1 | 3/2004 | Weinberg |
| 2004/0081669 A1 | 4/2004 | Greeven et al. |
| 2004/0158507 A1 | 8/2004 | Meek et al. |
| 2004/0178071 A1 | 9/2004 | Harrison et al. |
| 2004/0215486 A1 | 10/2004 | Braverman |
| 2004/0225528 A1 | 11/2004 | Brock |
| 2005/0014849 A1 | 1/2005 | Pettit et al. |
| 2005/0060171 A1 | 3/2005 | Molnar |
| 2005/0062603 A1 | 3/2005 | Fuerst et al. |
| 2005/0108044 A1 | 5/2005 | Koster |
| 2005/0125097 A1 | 6/2005 | Chudy et al. |
| 2005/0127176 A1 | 6/2005 | Dickinson |
| 2005/0149378 A1 | 7/2005 | Cyr et al. |
| 2005/0149414 A1 | 7/2005 | Schrodt et al. |
| 2005/0184151 A1 | 8/2005 | DiMaggio et al. |
| 2005/0283259 A1 | 12/2005 | Wolpow |
| 2005/0285732 A1 | 12/2005 | Sengupta et al. |
| 2005/0285746 A1 | 12/2005 | Sengupta et al. |
| 2006/0006999 A1 | 1/2006 | Walczyk et al. |
| 2006/0043177 A1 | 3/2006 | Nycz et al. |

(56) References Cited

U.S. PATENT DOCUMENTS

| | | |
|---|---|---|
| 2006/0043179 A1 | 3/2006 | Nycz et al. |
| 2006/0065726 A1 | 3/2006 | Andreasson et al. |
| 2006/0109105 A1 | 5/2006 | Varner et al. |
| 2006/0132311 A1 | 6/2006 | Kruest et al. |
| 2006/0145871 A1 | 7/2006 | Donati et al. |
| 2006/0152338 A1 | 7/2006 | Hsu |
| 2006/0152364 A1 | 7/2006 | Walton |
| 2006/0152367 A1 | 7/2006 | Narayanaswamy |
| 2006/0208886 A1 | 9/2006 | Beamer |
| 2006/0244593 A1 | 11/2006 | Nycz et al. |
| 2006/0267731 A1 | 11/2006 | Chen |
| 2007/0001809 A1 | 1/2007 | Kodukula et al. |
| 2007/0008399 A1 | 1/2007 | Botten et al. |
| 2007/0023512 A1 | 2/2007 | Miller et al. |
| 2007/0023513 A1 | 2/2007 | Andreasson et al. |
| 2007/0074722 A1 | 4/2007 | Giroux et al. |
| 2007/0114279 A1 | 5/2007 | Lessing et al. |
| 2007/0150382 A1 | 6/2007 | Danilewitz |
| 2007/0187475 A1 | 8/2007 | MacLeod |
| 2007/0188306 A1 | 8/2007 | Tethrake et al. |
| 2007/0200702 A1 | 8/2007 | Chung |
| 2007/0213659 A1 | 9/2007 | Trovato et al. |
| 2007/0213684 A1 | 9/2007 | Hickle et al. |
| 2007/0229268 A1 | 10/2007 | Swan et al. |
| 2007/0272746 A1 | 11/2007 | Ortiz et al. |
| 2008/0004908 A1 | 1/2008 | Oh et al. |
| 2008/0012687 A1 | 1/2008 | Rubinstein |
| 2008/0045930 A1 | 2/2008 | Makin et al. |
| 2008/0046295 A1 | 2/2008 | Albrecht |
| 2008/0061153 A1 | 3/2008 | Hickle et al. |
| 2008/0094214 A1 | 4/2008 | Azevedo et al. |
| 2008/0122878 A1 | 5/2008 | Keefe et al. |
| 2008/0128482 A1 | 6/2008 | Chen et al. |
| 2008/0129496 A1 | 6/2008 | Koblasz |
| 2008/0150722 A1 | 6/2008 | Jackson |
| 2008/0157967 A1 | 7/2008 | Jones et al. |
| 2008/0172253 A1 | 7/2008 | Chung et al. |
| 2008/0186180 A1 | 8/2008 | Butler et al. |
| 2008/0191013 A1 | 8/2008 | Liberatore |
| 2008/0218307 A1 | 9/2008 | Schoettle |
| 2008/0228160 A1 | 9/2008 | Harrison |
| 2008/0231456 A1 | 9/2008 | Matityaho |
| 2008/0243088 A1 | 10/2008 | Evans |
| 2008/0270178 A1 | 10/2008 | McRae et al. |
| 2008/0296373 A1 | 12/2008 | Smood et al. |
| 2008/0297356 A1 | 12/2008 | Oberle |
| 2008/0306772 A1 | 12/2008 | Shahrokh |
| 2008/0316045 A1 | 12/2008 | Sriharto et al. |
| 2009/0002173 A1 | 1/2009 | Bergsten et al. |
| 2009/0020442 A1 | 1/2009 | Dietrich et al. |
| 2009/0058653 A1 | 3/2009 | Geissler et al. |
| 2009/0144087 A1 | 6/2009 | Kelsch et al. |
| 2009/0153290 A1 | 6/2009 | Bierach |
| 2009/0164042 A1 | 6/2009 | Handfield et al. |
| 2009/0194987 A1 | 8/2009 | Christie et al. |
| 2009/0224891 A1 | 9/2009 | Vishik et al. |
| 2009/0231138 A1 | 9/2009 | Cheung et al. |
| 2009/0267740 A1 | 10/2009 | Pizzuto et al. |
| 2009/0267772 A1 | 10/2009 | Dehnadi |
| 2009/0277815 A1 | 11/2009 | Kohl |
| 2009/0294521 A1 | 12/2009 | De La Huerga |
| 2010/0022953 A1 | 1/2010 | Bochenko et al. |
| 2010/0022987 A1 | 1/2010 | Bochenko |
| 2010/0036310 A1 | 2/2010 | Hillman |
| 2010/0036678 A1 | 2/2010 | Bray |
| 2010/0036755 A1 | 2/2010 | Saghbini |
| 2010/0042439 A1 | 2/2010 | Martinez et al. |
| 2010/0079337 A1 | 4/2010 | Hsu et al. |
| 2010/0098425 A1 | 4/2010 | Kewitsch |
| 2010/0108761 A1 | 5/2010 | Nycz et al. |
| 2010/0114951 A1 | 5/2010 | Bauman et al. |
| 2010/0185458 A1 | 7/2010 | Calderwood et al. |
| 2010/0204659 A1 | 8/2010 | Bochenko |
| 2010/0217621 A1 | 8/2010 | Schoenberg et al. |
| 2010/0219097 A1 | 9/2010 | Ramasubramanian et al. |
| 2010/0238039 A1 | 9/2010 | Tethrake et al. |
| 2010/0268548 A1 | 10/2010 | Garrett et al. |
| 2010/0275625 A1 | 11/2010 | Lowenstein |
| 2010/0299158 A1 | 11/2010 | Siegel |
| 2010/0328474 A1 | 12/2010 | Hsieh |
| 2010/0332246 A1 | 12/2010 | Fedorko et al. |
| 2011/0006879 A1 | 1/2011 | Bartos |
| 2011/0060455 A1 | 3/2011 | Bogash et al. |
| 2011/0063091 A1 | 3/2011 | Kang |
| 2011/0068922 A1 | 3/2011 | Ross |
| 2011/0093279 A1 | 4/2011 | Levine et al. |
| 2011/0112682 A1 | 5/2011 | Matsukawa et al. |
| 2011/0115612 A1 | 5/2011 | Kulinets et al. |
| 2011/0125315 A1 | 5/2011 | Handfield et al. |
| 2011/0131056 A1 | 6/2011 | Chudy et al. |
| 2011/0139871 A1 | 6/2011 | Yturralde et al. |
| 2011/0161112 A1 | 6/2011 | Keefe et al. |
| 2011/0163871 A1 | 7/2011 | Einav et al. |
| 2011/0166878 A1 | 7/2011 | Louie et al. |
| 2011/0184751 A1 | 7/2011 | Holmes |
| 2011/0187549 A1 | 8/2011 | Balasing |
| 2011/0202174 A1 | 8/2011 | Bogash et al. |
| 2011/0225100 A1 | 9/2011 | Sangal et al. |
| 2011/0227722 A1 | 9/2011 | Salvat, Jr. |
| 2011/0240729 A1 | 10/2011 | Schuck |
| 2011/0257991 A1 | 10/2011 | Shukla |
| 2011/0270441 A1 | 11/2011 | Handfield et al. |
| 2011/0291809 A1 | 12/2011 | Niemiec et al. |
| 2011/0301446 A1 | 12/2011 | Kamen |
| 2011/0313395 A1 | 12/2011 | Krulevitch et al. |
| 2012/0037266 A1 | 2/2012 | Bochenko |
| 2012/0041778 A1 | 2/2012 | Kraft |
| 2012/0044054 A1 | 2/2012 | Hussain et al. |
| 2012/0061463 A1 | 3/2012 | Burke |
| 2012/0089411 A1 | 4/2012 | Srnka et al. |
| 2012/0089418 A1 | 4/2012 | Kamath et al. |
| 2012/0116798 A1 | 5/2012 | Heath et al. |
| 2012/0125994 A1 | 5/2012 | Heath et al. |
| 2012/0130534 A1 | 5/2012 | Wurm |
| 2012/0173440 A1 | 7/2012 | Becker et al. |
| 2012/0177256 A1 | 7/2012 | Keefe et al. |
| 2012/0179132 A1 | 7/2012 | Valk et al. |
| 2012/0185951 A1 | 7/2012 | Bauman et al. |
| 2012/0209619 A1 | 8/2012 | Knotts et al. |
| 2012/0240067 A1 | 9/2012 | Bauman et al. |
| 2012/0273087 A1 | 11/2012 | Einy et al. |
| 2012/0278096 A1 | 11/2012 | Holness |
| 2012/0278228 A1 | 11/2012 | Rubinstein |
| 2012/0323208 A1 | 12/2012 | Bochenko et al. |
| 2012/0325330 A1 | 12/2012 | Prince et al. |
| 2013/0018356 A1 | 1/2013 | Prince et al. |
| 2013/0035950 A1 | 2/2013 | MacDonald et al. |
| 2013/0038452 A1 | 2/2013 | Sawyer |
| 2013/0041784 A1 | 2/2013 | Danilewitz |
| 2013/0092727 A1 | 4/2013 | Edwards et al. |
| 2013/0105568 A1 | 5/2013 | Jablonski et al. |
| 2013/0151005 A1 | 6/2013 | Gerold et al. |
| 2013/0191149 A1 | 7/2013 | Kolberg et al. |
| 2013/0221082 A1 | 8/2013 | Botten |
| 2013/0221087 A1 | 8/2013 | Keefe et al. |
| 2013/0225945 A1 | 8/2013 | Prince et al. |
| 2013/0327822 A1 | 12/2013 | Keefe et al. |
| 2014/0060729 A1 | 3/2014 | Srnka et al. |
| 2014/0066880 A1 | 3/2014 | Prince et al. |
| 2014/0114472 A1 | 4/2014 | Bossi et al. |
| 2014/0117081 A1 | 5/2014 | Jablonski et al. |
| 2014/0136229 A1 | 5/2014 | Levine et al. |
| 2014/0142975 A1 | 5/2014 | Keefe et al. |
| 2014/0184390 A1 | 7/2014 | Elizondo, II |
| 2014/0184391 A1 | 7/2014 | Elizondo, II |
| 2014/0197954 A1 | 7/2014 | Caputo et al. |
| 2014/0210596 A1 | 7/2014 | Hussain et al. |
| 2014/0262919 A1 | 9/2014 | Hussain et al. |
| 2014/0263614 A1 | 9/2014 | Keefe et al. |
| 2014/0276213 A1 | 9/2014 | Bochenko |
| 2014/0282197 A1 | 9/2014 | Keefe et al. |
| 2014/0291397 A1 | 10/2014 | Caputo et al. |
| 2014/0367080 A1 | 12/2014 | Hussain et al. |
| 2014/0372145 A1 | 12/2014 | MacDonald et al. |

(56) References Cited

U.S. PATENT DOCUMENTS

| | | | |
|---|---|---|---|
| 2015/0058182 | A1 | 2/2015 | Kress-Spatz et al. |
| 2015/0235005 | A1 | 8/2015 | MacDonald et al. |
| 2015/0339622 | A1 | 11/2015 | MacDonald et al. |
| 2017/0132734 | A1 | 5/2017 | MacDonald et al. |
| 2018/0039758 | A1 | 2/2018 | MacDonald et al. |
| 2019/0088354 | A1 | 3/2019 | Yanowitz et al. |
| 2019/0272396 | A1 | 9/2019 | Clouser et al. |
| 2020/0013494 | A1 | 1/2020 | Caputo et al. |
| 2020/0167534 | A1 | 5/2020 | Elizondo, II |
| 2020/0357509 | A1 | 11/2020 | Gitchell et al. |
| 2021/0043291 | A1 | 2/2021 | James et al. |
| 2021/0383323 | A1 | 12/2021 | MacDonald et al. |
| 2022/0238219 | A1 | 7/2022 | MacDonald et al. |
| 2022/0282199 | A1 | 9/2022 | Vann |

FOREIGN PATENT DOCUMENTS

| | | |
|---|---|---|
| CN | 102791310 B | 12/2014 |
| EP | 2 496 283 | 9/2012 |
| IN | 2012/04914 P4 | 10/2013 |
| WO | WO 02/095675 | 11/2002 |
| WO | WO 03/071943 | 9/2003 |
| WO | WO 2006/026246 | 3/2006 |
| WO | WO 2006/135830 | 12/2006 |
| WO | WO 2010/074781 | 7/2010 |
| WO | WO 2011/056888 | 9/2011 |
| WO | WO 2011/115676 | 9/2011 |
| WO | WO 2011/150013 | 12/2011 |
| WO | WO 2013/082423 | 6/2013 |
| WO | WO 2013/116873 | 8/2013 |
| WO | WO 2013/134256 | 9/2013 |
| WO | WO 2014/159928 | 10/2014 |
| WO | WO 2014/189834 | 11/2014 |
| WO | WO 2015/026387 | 2/2015 |

OTHER PUBLICATIONS

Bacheldor, Beth, "ASD Healthcare Deploys RFID Refrigerated Drug Cabinets", RFID Journal, Sep. 24, 2007, p. 1. <http://www.rfidjournal.com/articles/view?3632>.

Bacheldor, Beth, "Cardinal Health Readies Item-Level Pilot", RFID Journal, May 31, 2006, p. 1. <http://www.rfidjournal.com/articles/view?2380>.

Bacheldor, Beth, "UCSD Medical Center Expands Its RFID Deployment", RFID Journal, Oct. 29, 2008, pp. 2. <http://www.rfidjournal.com/articles/view?4423>.

Bacheldor, Beth, "UMass Med Center Finds Big Savings Through Tagging", RFID Journal, Nov. 21, 2007, pp. 2. <http://www.rfidjournal.com/articles/view?3763/2>.

Barlas, Stephen, "Pharmacy Product Tracing Likely to Go National—Costs to Pharmacies Worrisome," Pharmacy & Therapeutics, Jan. 2009, vol. 34 No. 1, p. 14.

Baum, "How did RFID help University of MD Medical Center cut medication error rate?" Med City News, https://medcitynews.com/2013/12/rfid-help-university-md-medical-center-cut-medication-error-rate/?rf=1, Dec. 4, 2013, 2 Pages.

Becker et al., "SmartDrawer: RFID-Based Smart Medicine Drawer for Assistive Environments", Conference: Proceedings of the 2nd International Conference on Pervasive Technologies Related to Assistive Environments, PETRA 2009, Corfu, Greece, Jun. 9-13, 2009, pp. 8.

Belson, D., "Storage, Distribution, and Dispensing of Medical Supplies," CREATE Interim Report Under FEMA Grant EMW-2004-GR-0112, Apr. 21, 2005, pp. 1-36.

Bendavid et al., "Using RFID to Improve Hospital Supply Chain Management for High Value and Consignment Items", Procedia Computer Science, vol. 5, 2011, pp. 849-856.

Bendavid et al., "Redesigning the Replenishment Process of Medical Supplies in Hospitals with RFID", Business Process Management Journal, 2010, vol. 16, No. 6, pp. 991-1013.

Brown, Dennis E., "Rfid Implementation", McGraw-Hill Communications, 2007, Ch. 3 & 7 (portions), pp. 62-65, 81, 92-96, 106-113, 188-193 & 429.

Bryant, Blake, "Hacking SIEMs to Catch Hackers: Decreasing the Mean Time to Respond to Network Security Events with a Novel Threat Ontology in SIEM Software", Master's Thesis, University of Kansas, 2016, pp. 257.

Çakici et al., "Using RFID for the Management of Pharmaceutical Inventory-System Optimization and Shrinkage Control," Decision Support Systems, 2011, pp. 842-852.

Cangialosi et al., "Leveraging RFID in Hospitals: Patient Life Cycle and Mobility Perspectives", IEEE Applications & Practice, Sep. 2007, pp. 18-23.

Chao et al., "Determining Technology Trends and Forecasts of RFID by a Historical Review and Bibliometric Analysis from 1991 to 2005", Technovation, vol. 27, 2007, pp. 268-279.

Collins, "RFID Cabinet Manages Medicine", RFID Journal, Aug. 12, 2004, p. 1. <http://www.rfidjournal.com/articles/pdf?1081>.

CPG Sec. 400.210, Radiofrequency Identification Feasibility Studies and Pilot Programs for Drugs Nov. 2004 Compliance Policy Guide available at: <http://www.fda.gov/ICECI/ComplianceManuals/CompliancePolicyGuidanceManual/ucm074357.htm>.

"Crash Cart Inventory Checklist", Outpatient Surgery Magazine, Oct. 2004, p. 1. <http://www.outpatientsurgery.net/resources/forms/2004/pdf/OutpatientSurgeryMagazine_0410_crashCart.pdf>.

Curtin et al., "Making the 'MOST' out of RFID: a research agenda for the study of the adoption, usage and impact of RFID," Information Technology Management, Apr. 2007, pp. 87-110.

"Data Gathering Developments", Manufacturing Chemist, Feb. 1, 2005, p. 24. <https://www.manufacturingchemist.com/news/article_page/Data_gathering_developments/35805>.

Dutta et al., "RFID and Operations Management: Technology, Value, and Incentives", Production and Operations Management (POMS), vol. 16, No. 5, Sep.-Oct. 2007, pp. 646-655.

Edwards, John, "RFID Smart Shelves and Cabinets", RFID Journal, Aug. 24, 2009, pp. 4. <http://www.rfidjournal.com/articles/view?5140/4>.

*Electric Power Group v. Alstom, S.A.*, 830 F.3d 1350, 1353-54, 119 USPQ2d 1739, 1741-42 (Fed. Cir. 2016), pp. 12.

Epstein et al., "Development of a Scheduled Drug Diversion Surveillance System Based on an Analysis of Atypical Drug Transactions", Anesthesia and Analgesia, Oct. 2007, vol. 105, No. 4, pp. 1053-1060.

Erdem et al., "Investigation of RFID Tag Readability for Pharmaceutical Products at Item Level", Drug Development and Industrial Pharmacy, 2009, vol. 35, No. 11, pp. 1312-1324.

Fahrni, Jerry, "More RFID Refrigerator Stuff—Cubixx and myCubixx", Sep. 3, 2012, pp. 4. <http://jerryfahrni.com/2012/09/more-rfid-refrigerator-stuff-cubixx-and-mycubixx/>.

"Faraday Cage", Wikipedia, last edited Apr. 12, 2018, pp. 5. <https://en.wikipedia.org/wiki/Faraday_cage>.

Floerkemeier et al., "The Smart Box Concept for Ubiquitous Computing Environments", The Smart Box Concept for Ubiquitous Computing Environments, 2004, pp. 4.

Garza, Anyssa, "The Future of Pharmacy Medication Kit Storage", Pharmacy Times, https://www.pharmacytimes.com/contributor/anyssa-garza/2014/12/the-future-of-pharmacy-medication-kit-storage, Dec. 12, 2014, 2 Pages.

Glover et al., "RFID Essentials", O'Reilly Media, 2006, pp. 2, 14, 24, 31, 33, 107-110, 113-114, 117, 137-143, 162-169, 178-179.

Gonzalez, Stephanie, "Health Maintenance System (HMS) Hardware Research, Design, and Collaboration," NASA USRP—Internship Final Report, 2010, pp. 1-20.

Green, Kathryn, "Doing the Wave: Inventory Management with RFID", Diagnostic & Interventional Services, UMass Memorial Medical Center, Worcester, MA, vol. 15, No. 9, Sep. 2007, pp. 7. <https://www.cathlabdigest.com/articles/Doing-Wave-Inventory-Management-RFID>.

Harrop et al., "RFID for Healthcare and Pharmaceuticals, 2008-2018," Securing Pharma, May 2008, pp. 1-12.

Hawkins-Simons, "RFID Streamlines Refilling of Drug Trays", Pharmacy Technology Report, https://www.pharmacypracticenews.com/Pharmacy-Technology-Report/Article/03-14/RFID-Streamlines-Refilling-of-Drug-Trays/26159, Mar. 21, 2014, 9 Pages.

(56) References Cited

OTHER PUBLICATIONS

Ho et al., "A Prototype on RFID and Sensor Networks for Elder Healthcare: Progress Report", SIGCOMM '05 Workshops, Aug. 22-26, 2005, Philadelphia, PA, pp. 70-75.
Houliston, Bryan, "Integrating RFID Technology into a Drug Administration System," Bulletin of Applied Computing and Information Technology, vol. 3, No. 1, May 2005, pp. 8. Retrieved Sep. 26, 2013 from <http://citrenz.ac.nz/bacit/0301/2005Houliston_RFID.htm>.
Howard, JD, "Implementation of RFID in the Pharmaceutical Industry", Advisor: Dr. Jay Singh, California Polytechnic State University, San Luis Obispo, CA, Feb. 2009, pp. 11.
Humble, RN, Carol, "How RFID Freed Nurses From the Pain of Inventory Duties", Cath Lab Digest, Dec. 2009, vol. 17, No. 12. <https://www.cathlabdigest.com/articles/How-RFID-Freed-Nurses-From-Pain-Inventory-Duties>.
"Intel & Siemens Launch RFID Blood Bank in Malaysia", RFID Journal, Aug. 16, 2007, p. 1. <https://www.rfidjournal.com/articles/view?6801>.
Jones et al., "The Benefits, Challenges and Impacts of Radio Frequency Identification Technology (RFID) for Retailers in the UK", Marketing Intelligence & Planning, Mar. 2005, vol. 23, No. 4, pp. 395-402.
Jorgensen et al., "Executable Use Cases: Requirements for a Pervasive Health Care System," IEEE Software, Mar./Apr. 2004, pp. 34-41.
Juels, Ari, "RFID Security and Privacy: A Research Survey", IEEE Journal on Selected Areas in Communications, vol. 24, No. 2, Feb. 2006, pp. 381-394.
Kinsella, Bret, "Premier, Inc. Identifies Kit Check as 'Technology Breakthrough Product'—Awards exclusive agreement for pharmacy kit medication tracking solution", Press Release, https://kitcheck.com/2014/04/premier-inc-identifies-kit-check-technology-breakthrough-product-awards-exclusive-agreement-pharmacy-kit-medication-tracking-solution/, Apr. 2, 2014, 5 Pages.
KitCheck, Bluesight for Controlled Substances Overview, as retrieved Aug. 30, 2018 from https://web.archive.org/web/20180830001131/https://kitcheck.com/learn-more/video/bluesight-for-controlled-substances-overview/ in 1 page.
KitCheck, Diversion Events, as retrieved Aug. 30, 2018 from https://web.archive.org/web/20180830001851/https://kitcheck.com/solutions/controlled-substances/diversion-events/ in 3 pages.
KitCheck, "PharMEDium Prefilled Syringes with Kit Check: ASHP Symposium Summary", Jun. 2016, <https://kitcheck.com/wp-content/uploads/2016/06/pharmedium-prefilled-syringes-with-kit-check-download.pdf> in 9 pages.
KitCheck, Security, as retrieved Aug. 30, 2018 from https://web.archive.org/web/20180830000040/https://kitcheck.com/security/ in 1 page.
KitCheck, "St. Rita's Medical Center: 75% First-year ROI, Less Frustration", Case Study, 2016, <https://kitcheck.com/learn-more/case-study/st-ritas-medical-center/> in 2 pages.
Lahtela et al., "RFID and NFC in Healthcare: Safety of Hospitals Medication Care", 2008 Second International Conference on Pervasive Computing Technologies for Healthcare, Tampere, Finland, Jan. 30-Feb. 1, 2008, pp. 4.
Lai et al., "Enhancing Medication Safety and Reduce Adverse Drug Events on Inpatient Medication Administration using RFID," WSEAS Transactions on Communications, Oct. 2008, vol. 7, No. 10, pp. 1045-1054.
Lampe et al., "The Smart Box Application Model," Advances in Pervasive Computing, 2004, pp. 1-6.
Lewis, Mark O., "RFID-Enabled Capabilities and their Impact on Healthcare Process Performance", 31st International Conference on Information Systems, St. Louis, 2010, pp. 1-20.
Liu et al., "Point-of-Care Support for Error-Free Medication Process" (Jun. 25, 2007), retrieved Aug. 21, 2017, 12 pages, available at http://ieeexplore.ieee.org/document/4438162/.
McCall et al., "RMAIS: RFID-based Medication Adherence Intelligence System" (Aug. 31, 2010), retrieved Aug. 21, 2017, 4 pages, available at http://ieeexplore.ieee.org/document/5627529/.

"McKesson's Announces New Touch-Screen Driven Medication Dispensing Solution", Business Wire, Jun. 15, 2009, pp. 2, Available at: <http://www.businesswire.com/news/home/20090615005349/en/Mckesson-Announces-Touch-Screen-Driven-Medication-Dispensing-Solution#. VR7quPnF_10>.
"Medical Packaging Inc. Announces Clear Stem Flag Label System for Ampoules, Vials, and Syringes" Feb. 1, 2006 available at: <http://www.medpak.com/v1/news/20060201_CSFLAG.pdf>, in 1 page.
"Medication Tray Management" Pharmacy Purchasing & Products, Feb. 2018, pp. 18 & 20.
"Medication Tray Management" Pharmacy Purchasing & Products, Presentation, Nov. 2018, pp. 76 & 78.
"Medication Tray Management" Pharmacy Purchasing & Products, State of Pharmacy Automation, Aug. 2016, pp. 42 & 45.
"Medication Tray Management" Pharmacy Purchasing & Products, State of Pharmacy Automation, Aug. 2019, pp. 34-35.
Mehrjerdi, Yahia Zare, "RFID-Enabled Healthcare Systems: Risk-Benefit Analysis", International Journal of Pharmaceutical and Healthcare Marketing, 2010, vol. 4, No. 3, pp. 282-300.
Meiller et al., "Adaptive Knowledge-Based System for Health Care Applications with RFID-Generated Information", Decision Support Systems, vol. 51, 2011, pp. 198-207.
Mowry, Mike, "A Survey of RFID in the Medical Industry: With Emphasis on Applications to Surgery and Surgical Devices", MAE188, Introduction to RFID, Dr. Rajit Gadh, UCLA, Jun. 9, 2008, pp. 22.
"New RFID Medical Cabinets Deployed at 50 Hospitals", RFID Journal, Sep. 17, 2007, pp. 2. <https://www.rfidjournal.com/articles/view?6823>.
New et al., "Utilize ADC Transaction Data to Detect Diversion", Oct. 2017, vol. 14, No. 10, pp. 3, as retrieved from https://www.pppmag.com/article/2119/.
O'Connor, Mary Catherine, "Drug Distributor Uses RFID to Vend Meds", RFID Journal, May 23, 2006, pp. 2. <https://www.rfidjournal.com/articles/view?2363/2>.
O'Connor, Mary Catherine, "GlaxoSmithKline Tests RFID on HIV Drug", RFID Journal, Mar. 24, 2006, pp. 2. <https://www.rfidjournal.com/articles/view?2219/>.
O'Connor, Mary Catherine, "Interrogators Start to Evolve", RFID Journal, Jun. 1, 2006, pp. 3. <http://www.rfidjournal.com/purchase-access?type=Article&id=2398&r=%2Farticles%2Fview%3F2398>.
O'Connor, Mary Catherine, "Johnson & Johnson Finds Value in Multiple RFID Apps", RFID Journal, Apr. 23, 2008, pp. 2. <http://www.rfidjournal.com/articles/pdf?4046>.
O'Connor, Mary Catherine, "Mckesson Starts RFID Pilot for Viagra", RFID Journal, Feb. 17, 2005, pp. 2. <http://www.rfidjournal.com/articles/view?2157>.
O'Connor, Mary Catherine, "Pfizer Using RFID to Fight Fake Viagra", RFID Journal, Jun. 6, 2006, pp. 2. <http://www.rfidjournal.com/articles/pdf?2075>.
O'Connor, Mary Catherine, "To Keep Drugs from Expiring, Hospital Tests Intelliguard System", RFID Journal, Jan. 12, 2011, pp. 3. <http://www.rfidjournal.com/articles/view?8123>.
"ODIN Innovation Lab: EasyTunnel RFID", as posted Jul. 13, 2009, archived via archive.org <https://web.archive.org/web/20200316173502/https://www.youtube.com/watch?v=0rQhT4slQnw>, 1 page.
"ODIN RFID HQ Tour 2009", as posted Mar. 19, 2009, archived via archive.org <https://web.archive.org/web/20200316180429/https://www.youtube.com/watch?v=4Y4XIID0B_Y>, 1 page.
O'Driscoll et al., "RFID: An Ideal Technology for Ubiquitous Computing?" Dublin Institute of Technology School of Electronic and Communications Conference Papers, Jan. 1, 2008, pp. 1-17.
Pace et al., "Distributed Ambulatory Research in Therapeutics Network (DARTNet): Summary Report",Effective Health Care Research Reports, No. 14, Agency for Healthcare Research and Quality, Jul. 2009, pp. 41.
Pappu, Ph.D et al., "RFID in Hospitals: Issues and Solutions" Consortium for the Accelerated Deployment of RFID in Distribution, Sep. 2004, pp. 1-12.
Parida et al., "Application of RFID Technology for In-House Drug Management System", 15th International Conference on Network-Based Information Systems, 2012, pp. 577-581.

(56) References Cited

OTHER PUBLICATIONS

"RFID Medical Cabinets Evaluated in New Benchmark", RFID Journal, Sep. 12, 2007, pp. 2. <http://www.rfidjournal.com/articles/view?6819>.
Roberti, Mark, "RFID Basics for Health Care", RFID in Health Care, Produced by RFID Journal, Sep. 17, 2009, The Westin Waltham-Boston, Waltham, MA, pp. 33.
Saygin, C., "Adaptive Inventory Management Using RFID Data", The International Journal of Advanced Manufacturing Technology, 2007, vol. 32, pp. 1045-1051.
Singh et al., "Versatility of Radio Frequency Identification (RFID) Tags in the Pharmaceutical Industry", Instrumentation Science and Technology, vol. 36, pp. 656-663, 2008.
Summerfield, et al. "Evaluation of Medication Kit Processing Time Using Radio Frequency Identification (RFID) Technology", Innovations in Pharmacy, 2015, vol. 6, No. 2, Article 199, 7 Pages.
Swedberg, Claire, "North Carolina Hospital Identifies Recalled Drugs Via RFID", RFID Journal, http://www.rfidjournal.com/articles/view?10913, Aug. 14, 2013, 4 Pages.
Swedberg, Claire, "Tennessee Hospital Tracks High-Value Items", RFID Journal, Aug. 5, 2009, pp. 2. <http://www.rfidjournal.com/articles/view?5106>.
Swedberg, Claire, "Zimmer Ohio to Use RFID to Manage Orthopedic Products", RFID Journal, May 12, 2010, pp. 3. <https://www.rfidjournal.com/articles/pdf?7588>.
Tsai et al., "iMAT: Intelligent Medication Administration Tools" (Jul. 1, 2010), retrieved Aug. 21, 2017, 8 pages, available at http://ieeexplore.ieee.org/document/5556551/.
Tsai et al., "Smart Medication Dispenser: Design, Architecture and Implementation" (Sep. 27, 2010), retrieved Aug. 21, 2017, 12 pages, available at http://ieeexplore.ieee.org/document/5585838/.
Tzeng et al., "Evaluating the Business Value of RFID: Evidence from Five Case Studies," International Journal of Production Economics, 2008, vol. 112, pp. 601-613.
"UPM Raflatac UHF EPC Gen2 RFID in ODIN Solution at Johnson-Johnson DePuyIn-Q-Tel", as posted Jun. 10, 2009, archived via archive.org <https://web.archive.org/web/20200316174347/https://www.youtube.com/watch?v=JWGyR8Bgfl8>, 1 page.
"Vizient, Inc. Awards Kit Check Contract for Pharmacy Kit Medication Inventory Tracking and Replenishment", Press Release, http://www.prweb.com/releases/2016/09/prweb13691526.htm, Sep. 19, 2016, 3 Pages.
Wang et al., "Applying RFID Technology to Develop a Distant Medical Care Service Platform," International Journal of Electronic Business Management, 2010, vol. 8, No. 2, pp. 161-170.
Wang et al., "RFID Applications in Hospitals: A Case Study on a Demonstration RFID Project in a Taiwan Hospital", Proceedings of the 39th Hawaii International Conference on System Sciences, 2006, pp. 1-10.
Wasserman, Elizabeth, "Purdue Pharma to Run Pedigree Pilot", RFID Journal, May 31, 2005, pp. 2. <http://www.rfidjournal.com/articles/view?1626>.
Complaint, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Dec. 1, 2017, 45 pages.
Exhibit L; Fagron Academy, *Kit Check, Inc. v. Health Care Logistics, Inc.* (involving U.S. Pat. Nos.|8,990,099, 9,037,479, 9,058,412, 9,058,413, 9,367,665, 9,734,294, and 9,805,169), Case No. 2:17-cv-01041-ALM-CMV (S.D. Ohio), Dec. 1, 2017, 2 pages.
Defendant's Answer, Affirmative Defenses and Counterclaims to Plaintiff's Complaint, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jan. 2, 2018, 43 pages.
Plaintiff's Answer to Defendant's Counterclaims, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jan. 19, 2018, 14 pages.
Plaintiff Kit Check, Inc.'s Motion to Strike Insufficient Defenses, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jan. 19, 2018, 8 pages.
Defendant's First Amended Answer, Affirmative Defenses and Counterclaims to Plaintiff's Complaint, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Feb. 9, 2018, 43 pages.
Defendant's Memorandum in Opposition to Plaintiff Kit Check, Inc.'s Motion to Strike Insufficient Defenses, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Feb. 9, 2018, 6 pages.
Plaintiff's Answer to Defendant's First Amended Counterclaims, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Feb. 21, 2018, 14 pages.
Plaintiff Kit Check, Inc.'s Reply in Support of its Motion to Strike Insufficient Defenses, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Feb. 21, 2018, 6 pages.
Defendant Health Care Logistics, Inc.'s Motion for Judgment on the Pleadings Pursuant to Fed. R. Civ. P. 12(C), *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), May 25, 2018, 31 pages.
Exhibit A; U.S. Pat. No. 8,990,099, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), May 25, 2018, 12 pages.
Opinion & Order, *Kit Check, Inc. v. Health Care Logistics, Inc.* (involving U.S. Pat. Nos. 8,990,099,|9,037,479, 9,058,412, 9,058,413, 9,367,665, 9,734,294, and 9,805,169), Case No. 2:17-cv-01041-ALM-CMV (S.D. Ohio), Jun. 13, 2018, 9 pages.
Defendant Health Care Logistics, Inc's Invalidity Contentions Pursuant to Local Patent Rule 103.4, *Kit Check, Inc. v. Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jun. 18, 2018, 25 pages.
Exhibit 1; Initial Invalidity Claim Chart for U.S. Pat. No. 8,990,099, *Kit Check, Inc. v. Health Care Logistics, Inc.*, Case No. 2:17-cv-01041-ALM-CMV (S.D. Ohio), Jun. 18, 2018, 51 pages.
Exhibit 2; Initial Invalidity Claim Chart for U.S. Pat. No. 9,058,413, *Kit Check, Inc. v. Health Care Logistics, Inc.*, Case No. 2:17-cv-01041-ALM-CMV (S.D. Ohio), Jun. 18, 2018, 94 pages.
Exhibit 3; Initial Invalidity Claim Chart for U.S. Pat. No. 9,058,412, *Kit Check, Inc. v. Health Care Logistics, Inc.*, Case No. 2:17-cv-01041-ALM-CMV (S.D. Ohio), Jun. 18, 2018, 83 pages.
Exhibit 4; Initial Invalidity Claim Chart for U.S. Pat. No. 9,734,294, *Kit Check, Inc. v. Health Care Logistics, Inc.*, Case No. 2:17-cv-01041-ALM-CMV (S.D. Ohio), Jun. 18, 2018, 58 pages.
Exhibit 5; Initial Invalidity Claim Chart for U.S. Pat. No. 9,805,169, *Kit Check, Inc. v. Health Care Logistics, Inc.*, Case No. 2:17-cv-01041-ALM-CMV (S.D. Ohio), Jun. 18, 2018, 251 pages.
Exhibit 6; Initial Invalidity Claim Chart for U.S. Pat. No. 9,037,479, *Kit Check, Inc. v. Health Care Logistics, Inc.*, Case No. 2:17-cv-01041-ALM-CMV (S.D. Ohio), Jun. 18, 2018, 43 pages.
Exhibit 7; Initial Invalidity Claim Chart for U.S. Pat. No. 9,367,665, *Kit Check, Inc. v. Health Care Logistics, Inc.*, Case No. 2:17-cv-01041-ALM-CMV (S.D. Ohio), Jun. 18, 2018, 109 pages.
Plaintiff Kit Check, Inc.'s Memorandum in Opposition to Defendant Health Care Logistics, Inc.'s Motion for Judgment on the Pleadings, *Kit Check, Inc. v. Health Care Logistics, Inc.* (involving U.S. Pat.

(56) References Cited

OTHER PUBLICATIONS

Nos. 8,990,099, 9,037,479, 9,058,412, 9,058,413, 9,367,665, 9,734,294, and 9,805,169), Case No. 2:17-cv-01041-ALM-CMV (S.D. Ohio), Jun. 29, 2018, 35 pages.
Exhibit 1; Non-Final Office Action for U.S. Pat. No. 8,990,099, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jun. 29, 2018, 11 pages.
Exhibit 2; Notice of Allowance for U.S. Pat. No. 8,990,099, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jun. 29, 2018, 15 pages.
Exhibit 3; Non-Final Office Action for U.S. Pat. No. 9,367,665, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jun. 29, 2018, 12 pages.
Exhibit 4; Response to Non-Final Office Action for U.S. Pat. No. 9,367,665, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jun. 29, 2018, 18 pages.
Defendant Health Care Logistics, Inc.'s Reply in Support of Motion for Judgment on the Pleadings Pursuant to Fed. R. Civ. P. 12(C), *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jul. 20, 2018, 22 pages.
Exhibit A, *Kit Check, Inc.* v. *Health Care Logistics, Inc.* (involving U.S. Pat. Nos. 8,990,099, 9,037,479, |9,058,412, 9,058,413, 9,367,665, 9,734,294, and 9,805,169), Case No. 2:17-cv-01041-ALM-CMV (S.D. Ohio), Jul. 20, 2018, 43 pages.
Exhibit B; Plaintiff Kit Check, Inc.'s Disclosure of Asserted Claims and Infringement Contentions under Local Patent Rule 103.2, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jul. 20, 2018, 11 pages.
Plaintiff Kit Check, Inc.'s Motion to Strike Portions of Defendants' Reply or, in the Alternative, Motion for Leave to File a Sur-Reply, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Aug. 10, 2018, 6 pages.
Exhibit A; Plaintiff Kit Check, Inc.'s Sur-Reply in Opposition to Defendant's Motion for Judgment on the Pleadings, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Aug. 10, 2018, 5 pages.
Defendant Health Care Logistics, Inc.'s Memorandum in Opposition to Plaintiff Kit Check, Inc.'s Motion to Strike Portions of Defendant's Reply or, in the Alternative, Motion for Leave to File a|Sur-Reply, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Aug. 31, 2018, 6 pages.
Plaintiff Kit Check, Inc.'s Reply in Support of its Motion to Strike Portions of Defendant's Reply or, in the Alternative, Motion for Leave to File a Sur-Reply, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Sep. 14, 2018, 7 pages.
Joint Claim Construction and Prehearing Statement, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Sep. 20, 2018, 21 pages.
Plaintiff Kit Check, Inc.'s Opening Claim Construction Brief, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Nov. 16, 2018, 50 pages.
Exhibit 1; Disputed Claim Terms Chart, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Nov. 16, 2018, 4 pages.
Declaration of Jeffrey Fischer, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Nov. 16, 2018, 24 pages.
Defendant Health Care Logistics, Inc.'s Opening Claim Construction Brief, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Nov. 16, 2018, 32 pages.
Exhibit 1002; File History of U.S. Pat. No. 9,367,665, *Health Care Logistics, Inc.* v. *Kit Check, Inc.*, Case No. PGR2019-00022, Nov. 30, 2018, 256 pages.
Exhibit 1003; Expert Declaration, *Health Care Logistics, Inc.* v. *Kit Check, Inc.*, Case No. PGR2019-00022, Nov. 30, 2018, 9 pages.
Exhibit 1013; Claim Construction Brief (Defendant), *Health Care Logistics, Inc.* v. *Kit Check, Inc.*, Case No. PGR2019-00022, Nov. 30, 2018, 32pages.
Exhibit 1014; Claim Construction Brief (Plaintiff), *Health Care Logistics, Inc.* v. *Kit Check, Inc.*, Case No. PGR2019-00022, Nov. 30, 2018, 50 pages.
Petition for Inter Partes Review of U.S. Pat. No. 8,990,099, *Health Care Logistics, Inc.* v. *Kit Check, Inc.*, Case No. IPR2019-00376, Nov. 30, 2018, 42 pages.
Exhibit 1002; File History of U.S. Pat. No. 8,990,099, *Health Care Logistics, Inc.* v. *Kit Check, Inc.*, Case No. IPR2019-00376, Nov. 30, 2018, 557 pages.
Exhibit 1003; Expert Declaration, *Health Care Logistics, Inc.* v. *Kit Check, Inc.*, Case No. IPR2019-00376, Nov. 30, 2018, 9 pages.
Exhibit 1010; Claim Construction Brief (Defendant), *Health Care Logistics, Inc.* v. *Kit Check, Inc.*, Case No. IPR2019-00376, Nov. 30, 2018, 32 pages.
Exhibit 1011; Claim Construction Brief (Plaintiff), *Health Care Logistics, Inc.* v. *Kit Check, Inc.*, Case No. IPR2019-00376, Nov. 30, 2018, 50 pages.
Petition for Inter Partes Review of U.S. Pat. No. 9,058,412, *Health Care Logistics, Inc.* v. *Kit Check, Inc.*, Case No. IPR2019-00385, Nov. 30, 2018, 75 pages.
Exhibit 1002; File History of U.S. Pat. No. 9,058,412, *Health Care Logistics, Inc.* v. *Kit Check, Inc.*, Case No. IPR2019-00385, Nov. 30, 2018, 75 pages.
Exhibit 1003; Expert Declaration, *Health Care Logistics, Inc.* v. *Kit Check, Inc.*, Case No. IPR2019-00385, Nov. 30, 2018, 9 pages.
Exhibit 1013; Claim Construction Brief (Defendant), *Health Care Logistics, Inc.* v. *Kit Check, Inc.*, Case No. IPR2019-00385, Nov. 30, 2018, 32 pages.
Exhibit 1014; Claim Construction Brief (Plaintiff), *Health Care Logistics, Inc.* v. *Kit Check, Inc.*, Case No. IPR2019-00385, Nov. 30, 2018, 50 pages.
Petition for Inter Partes Review of U.S. Pat. No. 9,058,413, *Health Care Logistics, Inc.* v. *Kit Check, Inc.*, Case No. IPR2019-00387, Dec. 1, 2018, 73 pages.
Exhibit 1002; File History of U.S. Pat. No. 9,058,413, *Health Care Logistics, Inc.* v. *Kit Check, Inc.*, Case No. IPR2019-00387, Dec. 1, 2018, 549 pages.
Exhibit 1003; Expert Declaration, *Health Care Logistics, Inc.* v. *Kit Check, Inc.*, Case No. IPR2019-00387, Dec. 1, 2018, 9 pages.
Exhibit 1009; Children's Hospital Boston Joins Others Using RFID to Track Implantables, *Health Care Logistics, Inc.* v. *Kit Check, Inc.*, Case No. IPR2019-00387, Dec. 1, 2018, 3 pages.
Exhibit 1012; The "Orange Book", *Health Care Logistics, Inc.* v. *Kit Check, Inc.*, Case No. IPR2019-00387, Dec. 1, 2018, 1103 pages.

(56) References Cited

OTHER PUBLICATIONS

Exhibit 1013; Claim Construction Brief (Defendant), *Health Care Logistics, Inc.* v. *Kit Check, Inc.*, Case No. IPR2019-00387, Dec. 1, 2018, 32 pages.
Exhibit 1014; Claim Construction Brief (Plaintiff), *Health Care Logistics, Inc.* v. *Kit Check, Inc.*, Case No. IPR2019-00387, Dec. 1, 2018, 50 pages.
Petition for Inter Partes Review of U.S. Pat. No. 9,805,169, *Health Care Logistics, Inc.* v. *Kit Check, Inc.*, Case No. IPR2019-00388, Dec. 1, 2018, 76 pages.
Exhibit 1002; File History of U.S. Patent No. 9,805, 169, *Health Care Logistics, Inc.* v. *Kit Check, Inc.*, Case No. IPR2019-00388, Dec. 1, 2018, 286 pages.
Exhibit 1003; Expert Declaration, *Health Care Logistics, Inc.* v. *Kit Check, Inc.*, Case No. IPR2019-00388, Dec. 1, 2018, 9 pages.
Exhibit 1009; Claim Construction Brief (Defendant), *Health Care Logistics, Inc.* v. *Kit Check, Inc.*, Case No. IPR2019-00388, Dec. 1, 2018, 32 pages.
Exhibit 1010; Claim Construction Brief (Plaintiff), *Health Care Logistics, Inc.* v. *Kit Check, Inc.*, Case No. IPR2019-00388, Dec. 1, 2018, 50 pages.
Petition for Inter Partes Review of U.S. Pat. No. 9,367,665, *Health Care Logistics, Inc.* v. *Kit Check, Inc.*, Case No. IPR2019-00394, Dec. 3, 2018, 69 pages.
Exhibit 1002; File History of U.S. Pat. No. 9,367,665, *Health Care Logistics, Inc.* v. *Kit Check, Inc.*, Case No. IPR2019-00394, Dec. 3, 2018, 256 pages.
Exhibit 1003; Expert Declaration, *Health Care Logistics, Inc.* v. *Kit Check, Inc.*, Case No. IPR2019-00394, Dec. 3, 2018, 9 pages.
Exhibit 1013; Claim Construction Brief (Defendant), *Health Care Logistics, Inc.* v. *Kit Check, Inc.*, Case No. IPR2019-00394, Dec. 3, 2018, 32 pages.
Exhibit 1014; Claim Construction Brief (Plaintiff), *Health Care Logistics, Inc.* v. *Kit Check, Inc.*, Case No. IPR2019-00394, Dec. 3, 2018, 50 pages.
Plaintiff Kit Check, Inc.'s Notice of Filing Deposition Transcript of Jeffrey Fischer, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jan. 3, 2019, 3 pages.
Exhibit A; Deposition of Jeffrey Fischer, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jan. 3, 2019, 86 pages.
Plaintiff Kit Check, Inc.'s Responsive Claim Construction Brief, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jan. 3, 2019, 23 pages.
Exhibit A, *Kit Check, Inc.* v. *Health Care Logistics, Inc.* (involving U.S. Pat. Nos. 8,990,099, 9,037,479,|9,058,412, 9,058,413, 9,367,665, 9,734,294, and 9,805,169), Case No. 2:17-cv-01041-ALM-CMV (S.D. Ohio), Jan. 3, 2019, 43 pages.
Exhibit B; Deposition of Jeffrey Fischer, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jan. 3, 2019, 22 pages.
Defendant Health Care Logistics, Inc.'s Response to Plaintiff Kit Check, Inc.'s Opening Claim Construction Brief, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jan. 3, 2019, 22 pages.
Plaintiff Kit Check, Inc.'s Memorandum in Opposition to Defendant Health Care Logistics, Inc.'s Motion for Stay, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Feb. 11, 2019, 21 pages.
Exhibit 1; Defendant Health Care Logistics, Inc.'s Invalidity Contentions Pursuant to Local Patent Rule 103.4, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Feb. 11, 2019, 26 pages.
Defendant Health Care Logistics, Inc.'s Reply in Support of Motion for Stay, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Feb. 25, 2019, 10 pages.
Patent Owner's Preliminary Response, *Health Care Logistics, Inc.* v. *Kit Check, Inc.*, Case No. IPR2019-00376, U.S. Pat. No. 8,990,099, Mar. 8, 2019, 26 pages.
Patent Owner's Preliminary Response, *Health Care Logistics, Inc.* v. *Kit Check, Inc.*, Case No. IPR2019-00385, U.S. Pat. No. 9,058,412 B2, Mar. 8, 2019, 28 pages.
Patent Owner's Preliminary Response, *Health Care Logistics, Inc.* v. *Kit Check, Inc.*, Case No. IPR2019-00387, U.S. Pat. No. 9,058,413 B2, Mar. 13, 2019, 28 pages.
Patent Owner's Preliminary Response, *Health Care Logistics, Inc.* v. *Kit Check, Inc.*, Case No. IPR2019-00388, U.S. Pat. No. 9,805,169 B2, Mar. 13, 2019, 25 pages.
Patent Owner's Preliminary Response, *Health Care Logistics, Inc.* v. *Kit Check, Inc.*, Case No. IPR2019-00394, U.S. Pat. No. 9,367,668 B2, Mar. 13, 2019, 28 pages.
Opinion & Order, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Mar. 14, 2019, 17 pages.
Joint Stipulation of Partial Dismissal Without Prejudice, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Apr. 16, 2019, 2 pages.
Transcript of Markman Hearing Proceedings, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), May 6, 2019, 74 pages.
Decision Denying Institution of Inter Partes Review 35 U.S.C. § 314, *Health Care Logistics, Inc.* v. *Kit Check, Inc.*, Case No. IPR2019-00385, U.S. Pat. No. 9,058,412 B2, Jun. 3, 2019, 28 pages.
Decision Denying Institution of Inter Partes Review 35 U.S.C. § 314, *Health Care Logistics, Inc.* v. *Kit Check, Inc.*, Case No. IPR2019-00385, U.S. Pat. No. 9,805,169 B2, Jun. 3, 2019, 20 pages.
Decision Denying Institution of Inter Partes Review 35 U.S.C. § 314, *Health Care Logistics, Inc.* v. *Kit Check, Inc.*, Case No. IPR2019-00376, U.S. Pat. No. 8,990,099 B2, Jun. 4, 2019, 18 pages.
Decision Denying Institution of Inter Partes Review 35 U.S.C. § 314, *Health Care Logistics, Inc.* v. *Kit Check, Inc.*, Case No. IPR2019-00387, U.S. Pat. No. 9,058,413 B2, Jun. 7, 2019, 26 pages.
Decision Denying Institution of Inter Partes Review 35 U.S.C. § 314, *Health Care Logistics, Inc.* v. *Kit Check, Inc.*, Case No. IPR2019-00394, U.S. Pat. No. 9,367,665 B2, Jun. 11, 2019, 25 pages.
Stipulation and [Proposed] Order Granting Leave to Amend Plaintiff's Infringement Contentions and Defendant's Invalidity Contentions, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jul. 3, 2019, 3 pages.
Defendant Health Care Logistics, Inc.'s Motion for Leave to File Second Amended Answer, Affirmative Defenses, and Counterclaims, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Jul. 17, 2019, 5 pages.
Exhibit A; Defendant's Second Amended Answer, Affirmative Defenses, and Counterclaims to Plaintiff's Complaint, *Kit Check, Inc.* v. *Health Care Logistics, Inc.* (involving U.S. Pat. Nos. 8,990,099,

(56) References Cited

OTHER PUBLICATIONS 9,037,479, 9,058,412, 9,058,413, 9,367,665, 9,734,294, and 9,805,169), Case No. 2:17-cv-01041-ALM-CMV (S.D. Ohio), Jul. 17, 2019, 49 pages.
Request for Ex Parte Reexamination Under 35 U.S.C. 302-307 and 37 C.F.R. 1.510, U.S. Pat. No. 8,990,099 B2, U.S. Appl. No. 13/554,342, filed Jul. 25, 2019 in 80 pages.
Request for Ex Parte Reexamination Under 35 U.S.C. 302-307 and 37 C.F.R. 1.510, U.S. Pat. No. 9,058,412 B2, U.S. Appl. No. 14/603,730, filed Jul. 26, 2019 in 118 pages.
Request for Ex Parte Reexamination Under 35 U.S.C. 302-307 and 37 C.F.R. 1.510, U.S. Pat. No. 9,058,413 B2, U.S. Appl. No. 14/603,828, filed Jul. 25, 2019 in 151 pages.
Request for Ex Parte Reexamination Under 35 U.S.C. 302-307 and 37 C.F.R. 1.510, U.S. Pat. No. 9,805,169 B2, U.S. Appl. No. 14/701,958, filed Jul. 26, 2019 in 220 pages.
Request for Ex Parte Reexamination Under 35 U.S.C. 302-307 and 37 C.F.R. 1.510, U.S. Pat. No. 9,367,665 B2, U.S. Appl. No. 14/818,113, filed Jul. 26, 2019 in 164 pages.
Opinion & Order, *Kit Check, Inc.* v. *Health Care Logistics, Inc.* (involving U.S. Pat. Nos. 8,990,099, 9,037,479, 9,058,412, 9,058,413, 9,367,665, 9,734,294, and 9,805,169), Case No. 2:17-cv-01041-ALM-CMV (S.D. Ohio), Aug. 30, 2019, 26 pages.

\* cited by examiner

| Sept. 8, 2014 ▼ | My Inventory | Prep Syringes | My Patients | | Michael Jameson → 302 |
|---|---|---|---|---|---|
| | 304 | 306 | 308 | | |

Summary

Details

| By Drug 408 | | To Return | | | Submit |
|---|---|---|---|---|---|

| Item ~402 | | | | 404 ~ Volume | To Return 406 |
|---|---|---|---|---|---|
| Propofol 10mg/ml | | | | 20 mL | 8 |
| Fentanyl 50 mcg/ml | | | | 2 mL | 5 |
| Fentanyl 50 mcg/ml | | | | 5 mL | 5 |
| Hydromorphone 2mg/ml | | | | 1 mL | 6 |
| Morphine 10mg/ml | | | | 1 mL | 5 |
| Sufentanil 100 mcg | | | | 2 mL | 2 |
| Midazolam 1mg/ml | | | | 2 mL | 8 |
| Midazolam 1mg/ml | | | | 5 mL | 3 |

Midazolam 1mg/ml

Midazolam 1mg/ml

Sufentanil 100 mcg

Morphine 10mg/ml

Hydromorphone 2mg/ml

| My Patients | Prep Syringes | My Patients | Current: Jones, Abigail | | Michael Jameson |
|---|---|---|---|---|---|

Current Procedure
Jones, Abigail  22683925
2-19-1997  F

Completed Procedures
Hermosillo, Carlos  22683925
12-24-1945  M

Wu, Jenny  22683925
10-10-2008  F

Procedure Type: Ortho   Start: 14:10   Syncing with EMR...   Finish Procedure

| Drug | Initial | Admin. | Wasted | Rem. | To Waste |
|---|---|---|---|---|---|
| Hydromorphone 0.2 mg/ml | 2 mg | 0.6 mg | - | - | 1.4 mg |
| Propofol 10 mg/ml | 100 mg | 100 mg | - | - | - |
| Fentanyl 50 mcg/ml | 200 mcg | 250 mcg | - | - | - |
| Midazolam 1 mg/ml | 5 mg | 3 mg | - | - | 2 mg |

FIG. 5B

| Sept. 8, 2014 ▼ | My Inventory | Prep Syringes | My Patients | | Michael Jameson ▼ |
|---|---|---|---|---|---|
| Summary ❹ | | Summary | | | |
| Details | | | | 4 | Submit |
| | | To Waste | | to waste | |
| By Drug | | | | 23 to return | |
| Midazolam 1mg/ml | | Item | | Initial | To Waste |
| Midazolam 1mg/ml | | Fentanyl 50 mcg/ml | | 6 mL | 150 mcg |
| Sufentanil 100 mcg | | Hydromorphone 2mg/ml | | 1 mL | 1.4 mg |
| | | Midazolam 1mg/ml | | 1 mL | 2 mg |
| Morphine 10mg/ml | | To Return | | | |
| Hydromorphone 2mg/ml | | Item | | Initial | To Return |
| | | Propofol 10 mg/ml | | 20 mL | 2 |

FIG. 6

MEDICATION TRACKING

The present application is a continuation of U.S. patent application Ser. No. 17/177,914, filed on Feb. 17, 2021, entitled MEDICATION TRACKING, which is a continuation of U.S. patent application Ser. No. 16/822,459, filed on Mar. 18, 2020, entitled MEDICATION TRACKING, which is a continuation of U.S. patent application Ser. No. 16/103,001, filed Aug. 14, 2018, entitled MEDICATION TRACKING, which is a continuation of U.S. patent application Ser. No. 15/426,302, filed Feb. 7, 2017, entitled MEDICATION TRACKING, which is a continuation of U.S. patent application Ser. No. 14/876,533, filed Oct. 6, 2015, entitled MEDICATION TRACKING, which is a continuation of U.S. patent application Ser. No. 14/563,732, filed Dec. 8, 2014, entitled MEDICATION TRACKING, which claims priority to U.S. Provisional Patent App. No. 61/913,337, filed Dec. 8, 2013, entitled ENHANCED MEDICATION MANAGEMENT IN THE OPERATING ROOM ENVIRONMENT, U.S. Patent Provisional App. No. 62/000,570, filed May 20, 2014, entitled ANESTHESIA LABEL CREATION AND MIXTURE PREFERENCES SOLUTION, U.S. Patent App. No. 62/020,576, filed Jul. 3, 2014, entitled MULTI-DOSE INVENTORY SOLUTION, and U.S. Patent App. No. 62/062,845, filed Oct. 11, 2014, entitled ANESTHESIA CHECK; AUTOMATING AND IMPROVING THE WORKFLOW OF ANESTHESIA LABELING, ADMINISTRATION, AND INVENTORY RECONCILIATION, each of which is incorporated herein by reference in its entirety.

BACKGROUND

Pharmaceutical items (for example, drugs, diluents, medical and surgical supplies, gauze, scissors, needles, labels, baggies, bandages, packaging, vial, syringes, and/or other items that the pharmacy is responsible for), such as medications (for example, drugs, diluents, etc., in solid or liquid form), that have left a pharmacy of a medical care facility are to be managed closely to conform to regulatory guidelines regarding use and waste, to avoid misadministration and diversion, and to ensure appropriate inventory management and patient billing. In this context, medical care providers administer medications received from the pharmacy or removed from a crash cart or other pharmaceutical item storage unit. In some cases, prior to, or as part of, administration, the medical care providers transfer one or more medications from one medicinal container (for example, a vial, syringe, etc.) to another medicinal container and/or combine multiple medications into one medicinal container. As part of the transfer, the medical care provider prepares a handwritten label for the new medicinal container or new combination of medications in order to identify and track it throughout its lifecycle within the medical care facility. In addition, the medical care provider is responsible for returning unused medications (including any medications in the new medicinal container) from the original set of assigned pharmaceutical items, or reporting the administration, use, or waste of the medications, to the pharmacy for inventory management, billing, and regulatory control.

BRIEF DESCRIPTION OF THE DRAWINGS

FIG. 4 depicts an embodiment of a user interface for monitoring medications that are in the care of a particular medical care provider.

FIGS. 5A, 5B, and 5C depict embodiments of the user interface for monitoring the administration of medications to a particular patient.

FIG. 6 depicts an embodiment of a user interface for reconciling/wasting medications.

DETAILED DESCRIPTION

Figure 1A:
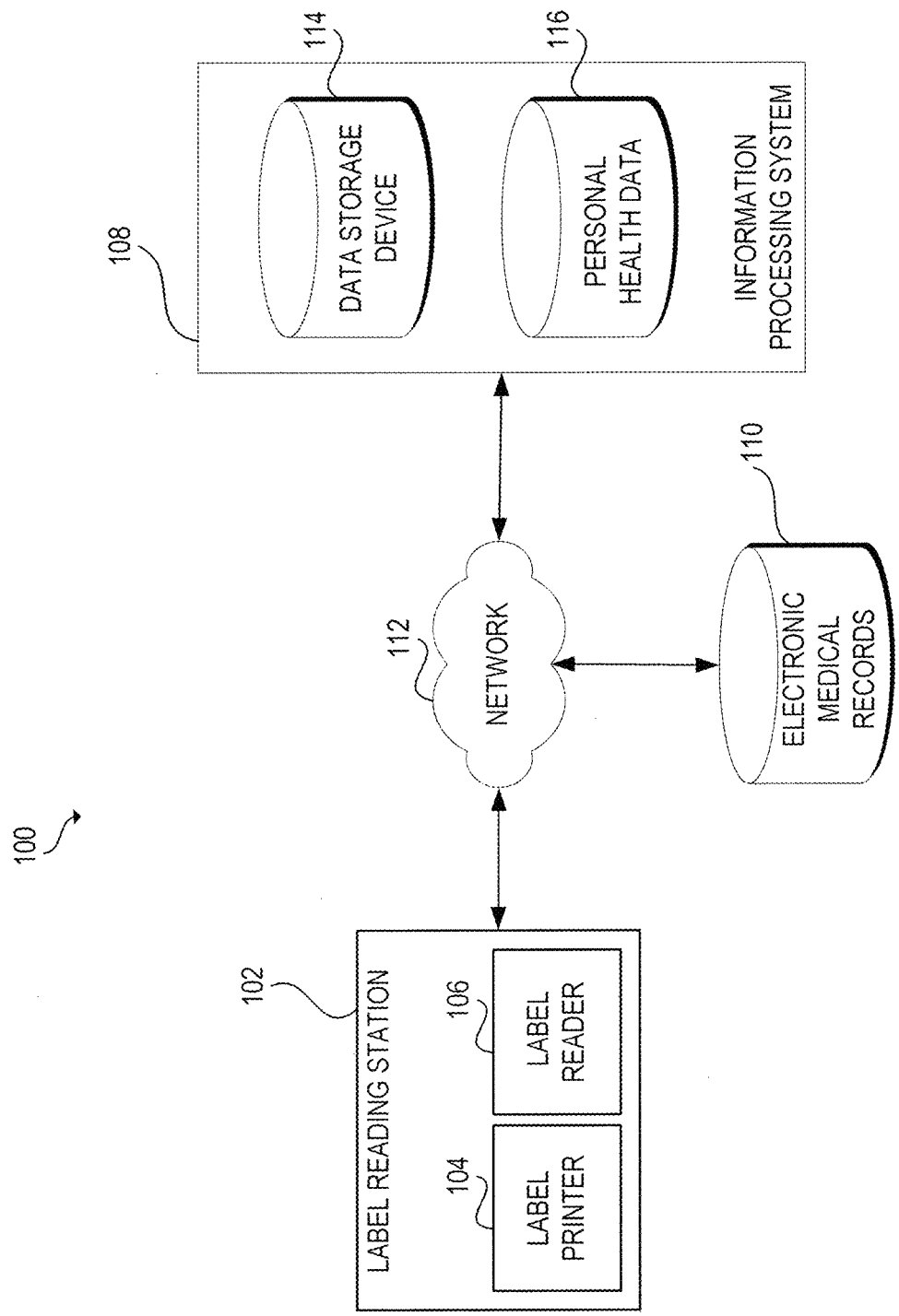
FIG. 1A is a block diagram illustrating an environment for tracking medications at a medical care facility.

System and methods are described herein for querying or reading machine-readable data from labels associated with medicinal containers, generating new labels with machine-readable data, and tracking the administration, waste, and return of medications in a medical care facility. Although various aspects of the disclosure will be described with regard to examples and embodiments, one skilled in the art will appreciate that the disclosed embodiments and examples should not be construed as limiting.

Parent/Child Medicinal Containers and Medications

In the present disclosure, reference is made to medicinal containers (which may also be referred to as medicinal packages), including parent and child medicinal containers, and medications, including parent and child medications. Examples of medicinal containers include, but are not limited to, vials, ampoules, IV bags, syringes, or other containers configured to store a medication, and the like.

A child medication can refer to a medication that results from an action, such as a transfer of a medication or combination of two or more medications. A parent medication can refer to the medication used in the action, such as a medication prior to combination with another (parent) medication or transfer. In addition, a child medicinal container can refer to a medicinal container that stores the child medication and/or a medicinal container into which medications are added and a parent medicinal container can refer to a medicinal container that stores parent medications and/or a medicinal container from which the medications in the child medicinal container were sourced.

Although referred to as parent and child medications and medicinal containers, it will be understood that a parent medicinal container (or parent medication) in one context may be a child medicinal container (or child medication) in another context. Similarly, a child medicinal container (or child medication) in one context may be a parent medicinal container (or parent medication) in another context. For example, if Fentanyl in a vial is transferred to a syringe, and then combined with sodium chloride in an IV bag, the Fentanyl in the syringe can be referred to as a child medication as part of the transfer to the syringe and as a parent medication as part of the combination with the sodium chloride in the IV bag. Similarly, the syringe can be referred to as a child medicinal container as part of the Fentanyl transfer to the syringe and as a parent medicinal container as part of the combination of the Fentanyl with the sodium chloride in the IV bag.

In some cases, a child medicinal container may be a previously unused medicinal container and/or have a single parent medicinal container. Similarly, a child medication may have a single parent medication. For example, if Propofol is removed from a vial and added to a syringe, the vial can be considered the parent medicinal container and the syringe can be considered the child medicinal container and/or the Propofol in the vial can be considered the parent medication and the Propofol in the syringe can be considered the child medication. In such cases, the syringe may have been previously unused, used with the same patient, or sterilized prior to the addition of the Propofol.

In certain cases, the child medicinal container may have multiple parent medicinal containers and may even be the same as one of the parent medicinal containers. Similarly, a child medication may have multiple parent medications. For example, if Fentanyl from one vial and sodium chloride from another vial are combined into a syringe, the vials can be referred to as the parent medicinal containers and the syringe can be referred to as the child medicinal container and/or the Fentanyl and sodium chloride in the vials can be referred to as the parent medications and the combined Fentanyl and sodium chloride in the syringe can be referred to as the child medication.

In some scenarios, the child medicinal container can be the same as one of the parent medicinal containers. For example, if Fentanyl is in a syringe and sodium chloride is added to the syringe from a vial, the vial can be referred to as a parent medicinal container and the syringe can be referred to as a parent medicinal container and the child medicinal container. Similarly, the Fentanyl in the syringe prior to the combination and the sodium chloride in the vial prior to the combination can be referred to as the parent medications and the combined Fentanyl and sodium chloride in the syringe can be referred to as the child medication.

It will be understood that the system can track child/parent medicinal containers and/or child/parent medications, as desired. Accordingly, the examples used above and throughout the description should not be construed as limiting. Furthermore, it will be understood that the system can track any pharmaceutical item and is not limited to tracking medicinal containers and/or medications.

System Overview

The system described herein can be used for the identification and lifecycle tracking of medicinal containers within the medical care facility environment, and can enhance the identification and lifecycle tracking of medications that have left the medical care facility pharmacy. Child medications or medicinal containers created outside the pharmacy (for example, at a crash cart, in a patient room, or in the operating room) can be tagged using RFID technology or a serialized number, or barcode, so that the child medication or child medicinal container as well as any parent medications or parent medicinal containers assigned to the medical provider can be available in the pharmacy's inventory for reconciliation, regulatory reporting, and as overall inventory management. In some instances, users may be barred from creating labels for child medications or medicinal containers that do not follow rules defined by the hospital and regulatory agencies, or for medications to which the user does not have permissions.

In addition, the system can allow users to indicate administration and non-administration of medications and other pharmaceutical items provided by the pharmacy or elsewhere, or items created by the provider. By enforcing rules regarding the combination of medications, such as drugs and/or diluents, and creation of child medications or medicinal containers, and enhancing the existing reconciliation workflow of providers in the medical care facility, the system can be used to create reports for use by the pharmacy and hospital for patient billing, detection and elimination of medication diversion, detection and elimination of medication misadministration and misuse, and other procedural errors or inefficiencies.

In some embodiments, the system can rely on data specific to each pharmaceutical inventory item (for example, medicinal containers, such as vials, ampoules, IV bags, and syringes, gauze, medical supplies, etc.) originating in the pharmacy or created by the user within the medical care facility environment. This data can be captured by reading data encoded on RFID tags present on each item or alternatively by scanning a serialized barcode or QR code, or other technology, etc. The system can create RFID or serialized barcode tags for placement on child medicinal containers, and can provide the user with the ability to indicate the administration of medication and/or the disposal of medication.

Although described above with reference to identification and lifecycle tracking of pharmaceutical items in the medical care facility environment, it will be understood that the system can also be used to enforce adherence to regulations regarding creation of child medications or medicinal containers as well as proper administration of medications, such as disallowing the use of expired medications and medications from manufacturer lots and/or medical care facility lots that have been recalled, and providing warnings, such when a syringe has already been used by another patient.

Pharmaceutical items, such as medicinal containers, are processed in several different stages before being distributed to locations inside the hospital such as smaller satellite pharmacies, dispensing stations, and pre-prepared groups of medications in kits and trays. The system described herein can track the location and custody of pharmaceutical items throughout these locations, and into the patient administration environment. Once inside the patient administration environment, the system can enforce rules regarding the creation, administration, and reconciliation of both new and preexisting pharmaceutical items.

In the patient administration environment, the system can use a handheld, tablet, or desktop device used to interact with the user, an RFID reader (or barcode or QR code reader) to identify the pharmaceutical items, and a printer used to create RFID or serialized tags for pharmaceutical items created within the patient administration environment.

The system can further include a graphical user interface, an application programming interface, a database containing pharmaceutical items, user information, data related to hospital-specific workflows and rules, log entries for pharmaceutical item history, custody, location, administration, and other data, and an application that sends data to the printer for the creation of standards-compliant pharmaceutical labels for items created in the operating room environment.

The system can further record the physical location of items within a hospital or medical center campus, and the possession of items by specific users. The system can use both physical checkpoints such as RFID readers, and workflow checkpoints to record the location of a pharmaceutical item. For example, an RFID tag with a specific unique identifier can be coupled to a 10 mL vial of Fentanyl, which is a DEA Schedule II controlled substance. The unique identifier can be used to store data regarding the Fentanyl and/or the vial in the database used by the system. As the vial (and Fentanyl) physically moves throughout the medical care facility, RFID readers throughout the medical care facility can record the physical movement and note the location and time that the RFID tag of that pharmaceutical item was read.

Medicinal Container Tracking

Before the vial (and medication) leaves a pharmacy, the system can facilitate the custody assignment of that vial (and medication) to a specific user and can record the user in possession of the item, in a specific place, and at a specific time. Tracking the chain of custody can continue in the patient administration environment, as the medication can be administered directly to the patient (either partially or in its entirety), can be discarded into a waste receptacle (either partially or in its entirety), can be returned to the pharmacy (either partially or in its entirety), or can be used to create a child medication or child medicinal container in the operating room, or elsewhere (either partially or in its entirety).

The system can track these additional movements and transformations, including any other assignments of custody that might occur within the patient administration context, such as assigning custody to another provider to complete a work shift or patient case or procedure. To assign custody to another provider the custodian provider can scan a badge or otherwise self-identify to the system. The provider can then scan the medications (separately or collectively) that are to change custody. The receiving provider can similarly self-identify to the system and indicate to the system that they are taking custody. The system can verify the status of the medications (for example, expiration, amounts, etc., as described in greater detail below). In addition, the system can verify that the receiving provider has the appropriate privileges to receive the medications.

Additionally, the system can enforce the rules of the medical care facility by requiring one or more approval actions for changes in custody as well as one or more approval actions for user indications of administration or waste actions. For example, the system can allow a provider to indicate they have discarded a pharmaceutical item into a waste receptacle, and if the medical care facility rules dictate that action must be verified by another user, the system can provide the interface and logging mechanism for the witness to verify the action, either through manual interaction with a graphical user interface or by the system reading user information which may come from an RFID-enabled badge or some other authentication method.

The tracking mechanisms of the system can pertain to pharmaceutical items compounded elsewhere on-site or within the patient administration environment. The system can provide a detailed history of pharmaceutical items used in a patient administration environment regardless of their origin, by capturing a snapshot of the package and its contents as it exists over time. The data capture can enable the system to provide a clear picture into the movement of medications through medicinal containers. In turn, the system can allow staff members to locate any pharmaceutical item that has been identified as problematic, such as expired or recalled medication, regardless of whether it has been assigned to a user or a physical location, administered to a patient, discarded into a waste receptacle, or used in the creation of a child medication or child medicinal container.

For example, in the patient administration environment an anesthesiology provider may have custody of a vial of Vecuronium bromide powder and a vial of normal saline. The provider can create a child medication or child medicinal container that combines an amount of Vecuronium bromide powder in milligrams with an amount of normal saline in milliliters. The system can handle the combination of pharmaceutical items of different types, and can produce a child medication or child medicinal container of the appropriate type. In the example above, the system can determine that the combination of a powder and a liquid creates an item that is a mixture, combining two liquids results in another liquid, and combining two mixtures results in another mixture.

Similarly, the system can determine the appropriate unit of measure from the combination of pharmaceutical items measured in different units. In the example above, a powder measured in milligrams combined with a liquid measured in milliliters results in a mixture measured in milligrams over milliliters. Similarly, a liquid measured in milliliters combined with another liquid measured in milliliters, results in a new liquid measured in milliliters, and so on.

New Label Creation

As part of the process of physically combining items, the provider can use the system to create an RFID label (or barcode or QR code label) to place on the child medicinal container, which the system can use to track location, custody, and administration of the contents of the child medicinal container ("Vecuronium bromide in Normal Saline"), or child medication, alongside the two parent medications or parent medicinal containers ("Vecuronium bromide" and "Normal Saline"). The system can automatically create a new expiration date for the child medication and/or child medicinal container based on rules set by the medical care facility, or otherwise, and automatically calculate the volume of the contents within the child medicinal container, or child medication. The system can also update the quantity of the parent medicinal containers, or parent medications, as wells the expiration of the parent medications or parent medicinal containers to reflect that a sterile barrier has been pierced. The system can block a provider from creating child medications or child medicinal containers from expired or recalled sources, and it may not allow the provider to create child medications or child medicinal containers outside of rules established by the medical care facility, which includes the number of different items within one child medicinal container as well as specific medicinal combinations. Once the label has been created and placed on the child medicinal container, the system can associate the label with the child medication or child medicinal container and assign custody to the provider.

The provider can use the system in the same way to produce another distinct child medication or child medicinal container of "Vecuronium bromide in Normal Saline" from the same parent medications or parent medicinal containers used to create the first child medication or child medicinal container. In this case, the system can record both children of the parent medications or parent medicinal containers, and track the location, custody, and administration of all of the medications or medicinal containers separately. The system allows for the creation and tracking of multiple generations of pharmaceutical items. For instance, if a provider takes the second generation "Vecuronium bromide in Normal Saline" item and combines it with a large bag of normal saline for use in an IV drip, the system can create another RFID label for the third-generation medication or medicinal container and track its custody, location, and administration accordingly. Should the medical care facility or pharmacy need to account for every milligram of Vecuronium bromide from a specific manufacturer's lot, the system can enable them to find not only unused vials on pharmacy shelves, but syringes drawn up in the patient administration context, as well as bags of solution containing the contents of syringes drawn up in the patient administration context.

The system can also be configured to track amounts of medications moving between items. For example, a provider may want to fill three syringes with a DEA Class 2 drug, such as Fentanyl, but may not indicate the actual amounts transferred from each vial, and may simply "administer" a syringe rather than record partial use. At some point, the provider reconciles how much Fentanyl was used, administered, and wasted. The system can record all of the parent medications or medicinal containers where Fentanyl came from and can also record all of the child medications or medicinal containers, such as destination syringes or bags, as well as the cases, rooms and waste bins where any of the medicinal containers may have been placed. Accordingly, the actual reconciliation of how much Fentanyl was used, wasted, and returned can be reconciled at some later point in time without knowing the exact volumes of drugs in each item along the way.

Reconciling Medications

The system can also provide an efficient mechanism for reconciling the administration and waste of pharmaceutical items in a patient administration context. Through the use of RFID or serialized labels on the pharmaceutical items, the provider can scan these items in bulk and perform one action on all of the items scanned, or can scan items individual and perform more granular actions. For example, at the end of a medical case in the operating room, the provider may have ten empty syringes to reconcile. If all of the syringes are empty and the provider intends to place them all in a waste receptacle, the system can scan the group of items. The system can identify all items scanned and allows the user to indicate the amount used (e.g. "all") and intention (e.g. "discard"), which is then applied to all of the scanned items. The system can also record partial amounts used or wasted of single medicinal containers (e.g. "10 mL used and 15 mL wasted from a 25 mL package"). The system allows for medical care facilities to specify the intentions they would like to track as well as rules regarding item administration and reconciliation, which includes the units of measure used to record administration and waste and whether to record mass versus volume of an item. In addition to the manual reconciliation of administration and waste of items, the system can interact with patient electronic medical record stored in systems accessible within the patient administration context. The system can send data regarding syringe contents, as well as receive data regarding actual use from the patient's electronic medical records.

Restocking

The system can use the data captured within the patient administration environment not only for reports within this environment but also for reports used in the pharmacy and medical care facility overall. Using the data captured in the location and custody tracking features, the system can provide reports indicating drawers and cabinets in specific locations to be restocked due to expired, empty, recalled, or otherwise incorrect inventory. In addition, the system can cause a display to display the inventory of a particular drawer or cabinet. Furthermore, as part of the restocking, the system can query the RFID or serialized labels on the new items, update the database accordingly, and report the correct state of the pharmaceutical and supply items in a particular location and as verified by the user. The system can additionally provide detailed reports on pharmaceutical and supply items assigned to a user, to a room, or to a patient case, and the end result of each of those items, thus clearly showing where pharmaceutical items such as controlled medications have been misused or lost. Beyond the day-to-day workflow of tracking drugs, the data captured within the system can be used for pattern detection of different events or situations such as diversion patterns, over and under administration of drugs by a provider, over or under billing of patients, pharmaceutical and supply order optimization, warning and calculation of waste and the impact on the water supply and other predictive measures.

Tracking Environment

FIG. 1A is a block diagram illustrating an environment 100 for tracking medications at a medical care facility. In the illustrated embodiment, the environment 100 includes a label reading station 102 communicatively coupled with an information processing system 108 and an electronic medical records database 110. The label reading station 102 can be communicatively coupled directly with the information processing system 108 and/or the electronic medical records database 110, such as via a wired or wireless connection, or can be communicatively coupled via a network 112. The network 112 can be a local area network or a wide area network, such as the internet, etc.

The label reading station 102 can be located in any location of a medical care facility, such as on a particular floor, in a particular wing, in an operating room, patient room, or other patient administration environment. In some embodiments, multiple label reading stations 102 can be located throughout a medical care facility, such as in different patient rooms, operating rooms, etc.

In the illustrated embodiment, the label reading station 102 includes a label printer 104 and a label reader 106. In some embodiments, the label printer 104 and the label reader 106 can be implemented as an RFID label printer and an RFID label reader, respectively. In certain embodiments, the label printer 104 and the label reader 106 can be implemented using a variety of technologies, such as a bar code reader and printer, QR code reader and printer, etc.

When implemented using barcode or QR code technology, the label reader 106 can be configured to capture an image of a barcode or QR code and/or emit a laser that can capture the barcode or QR code data. When implemented using RFID technology, the label reader 106 can be configured to emit an electromagnetic wave, such as a radio wave, that activates one or more RFID tags in proximity to the label reader 106. The emission of the electromagnetic wave can also be referred to as a query. In some embodiments, the RFID tags used in conjunction with the label reading station 102 can be passive or active RFID tags.

The electromagnetic wave emitted by the label reader 106 can cause the RFID tags to generate a response that includes data stored on the RFID tag. Upon receiving the data from the RFID tag, the label reading station 102 can communicate with the information processing system 108 and/or the electronic medical records database 110 to process the data.

In some scenarios, as part of the processing, the label reading station 102 can generate a label to be affixed to a medicinal container. The label printer 104 can be used to print the new label. In some embodiments, the new label can include an RFID tag that has stored thereon a unique identifier. In certain embodiments additional information can be stored on the RFID tag, such as medication name data, expiration data, provider data, patient data, etc. In some embodiments, the label printer 104 prints information regarding the medication onto the RFID tag. Some non-limiting embodiments of labels that can be printed by the label printer 104 are described in greater detail below with respect to FIGS. 2A and 2B. In certain embodiments, the label printer 104 can be configured to print the RFID tag or print onto a label that already includes an RFID tag. Similarly, in some embodiments, the label printer 104 can be configured to print a bar code or QR code and/or print onto a label that already includes a bar code or QR code.

Although the illustrated embodiment shows the label reading station 102 as including a label printer 104 and a label reader 106, it will be understood that in some embodiments the label reading station 102 may include fewer or more components. For example, in some scenarios, the label reading station 102 can omit the label printer 104. In such embodiments, the label reading station 102 can be placed at or near a location where a medication is being administered to a patient. In such situations, a medical care provider can place a label near the label reading station 102, which can be read by the label reader 106. The label reading station 102 can then transmit the information to the information processing system 108 for processing. Accordingly, the information processing system 108 can update the medical records of the particular patient with data regarding the administration of the medication, determine whether a particular medication has been provided to a patient located at or near the label reading station 102, determine whether the medicinal container has been used previously, etc. In some embodiments the label reading station 102 can be implemented as a portable or handheld device that can be used to quickly and easily read RFID tags.

Furthermore, although reference is made throughout the specification to the label reading station 102 performing various analytical or processing functions, it will be understood that, in some embodiments, the information processing system 108 performs these functions, and the label reading station 102 is used to acquire data from one or more labels, display data based on data and/or instructions received from the information processing system 108, and print a label based on data and/or instructions received from the information processing system 108. In such embodiments, the label reading station 102 can receive notifications of processing functions performed by the information processing system 108, such as indications of the verification of a medication and/or indications regarding associations between any combination of medications, medicinal containers, unique identifiers, medical providers and/or patients, etc. Accordingly, in some embodiments, the amount of processing performed by the label reading station 102 can be reduced and/or minimized, and the label reading station 102 can act as a conduit to the information processing system 108. In this way, the hardware requirements and costs of the label reading station 102 can be reduced in favor of a larger or more robust information processing system 108. In certain embodiments, the label reading station 102 can include the information processing system 108 and perform all of the functions described herein.

The information processing system 108 can include one or more microprocessors, a data storage device 114, a personal health data storage device 116, and a network interface for communication over the network 112. In some embodiments, the information processing system 108 can be implemented as a server or workstation located at a remote facility or at the same medical care facility. The data storage device 114 can include information regarding medications and pharmaceutical items used in the environment 100, user that are allowed to use the label reading station 102, account information for individual medical care facilities, audit information, reports, logs, and various rules with regards to the medications, etc.

The rules can include information regarding which medications can be used with each other, preferences for different users, how to calculate expiration dates for medications, substitute medications that can be used in place of other medications, drug policies, etc. Using the information received from the label reading station 102 and data in the data storage device 114, the information processing system 108 can verify the status of the medications, calculate expiration dates for the medications, determine whether a medication has been recalled or is expired, provide mixing or dilutions suggestions, associate medications, RFID tags, and/or unique identifiers with medical care providers and/or patients, generate restocking notifications, create new database entries for new medications and/or new RFID tags, track drug administration and/or reconciliation, generate reports regarding drug administration by various providers, reports regarding drug administration to different patients, etc.

The personal health data storage device 116 can include personal health information of the patients at a medical care facility, similar to that stored in the electronic medical records database 110. In some embodiments, the personal health data storage device 116 stores a subset of the data from the electronic medical records database 110, such as gender, allergic reactions, and medications received, etc. In certain embodiments, the personal health data storage device 116 is a copy of the electronic medical records database 110. In some cases, the personal health data storage device 116 can include data from multiple electronic medical records databases 110 from various medical care facilities.

Furthermore, as data in the personal health data storage device 116 is changed by the information processing system 108, a similar change can be made in the electronic medical records database 110. Similarly, changes to the electronic medical records database 110 can be updated in the personal health data storage device 116. In this way, the personal health data storage device 116 and electronic medical records database 110 can be synched.

In some cases, additional requirements are placed on databases that store patient identifying data. Accordingly, in some embodiments, the data storage device 114 can be implemented separately from the personal health data storage device 116, as either a separate database and/or on a distinct data storage device. However, it will be understood that in certain embodiments, the data storage device 114 and personal health data storage device 116 can be implemented as part of the same database and/or on the same storage device.

When implemented separately, the data storage device 114 can include a unique identifier for each patient that does not include personal health data. For example the unique identifier can be a unique number or other identifier. When the data storage device 114 desires to access personal health data, it can use the unique identifier to communicate with the personal health data storage device 116. In this way, the personal health information can be separated from non-personal health information.

Furthermore, in some embodiments, the information processing system 108 can omit the personal health data storage device 116. For example, in some cases a particular medical care facility may prefer not to have a copy of personal health information stored outside the electronic medical records database 110. In such embodiments, the information processing system 108 can omit the personal health data storage device 116.

The electronic medical records database 110 can include patient specific information, such as gender, age, medical history, medications taken, allergies, weight, medical procedures, vital signs, audit info, and whatever other information a medical care provider desires. The electronic medical records information from the electronic medical records database 110 can be used in conjunction with the rules in the data storage device 114 of the information processing system 108 to determine which medications can be provided to a patient and generate labels at the label reading station 102.

In certain embodiments, the label reading station 102, the information processing system 108, and/or the electronic medical records database 110 can implemented in a single device. In some embodiments, the information processing system 108 and/or the electronic medical records database 110 can be remotely located from the label reading station 102. For example, the electronic medical records database 110 and the information processing system 108 can be located at a different site from the medical care facility. In some embodiments, electronic medical records database 110 and the information processing system 108 can be proximally located at the same medical care facility, such as in the same room or floor of the medical care facility.

Figures 1B, 1C:
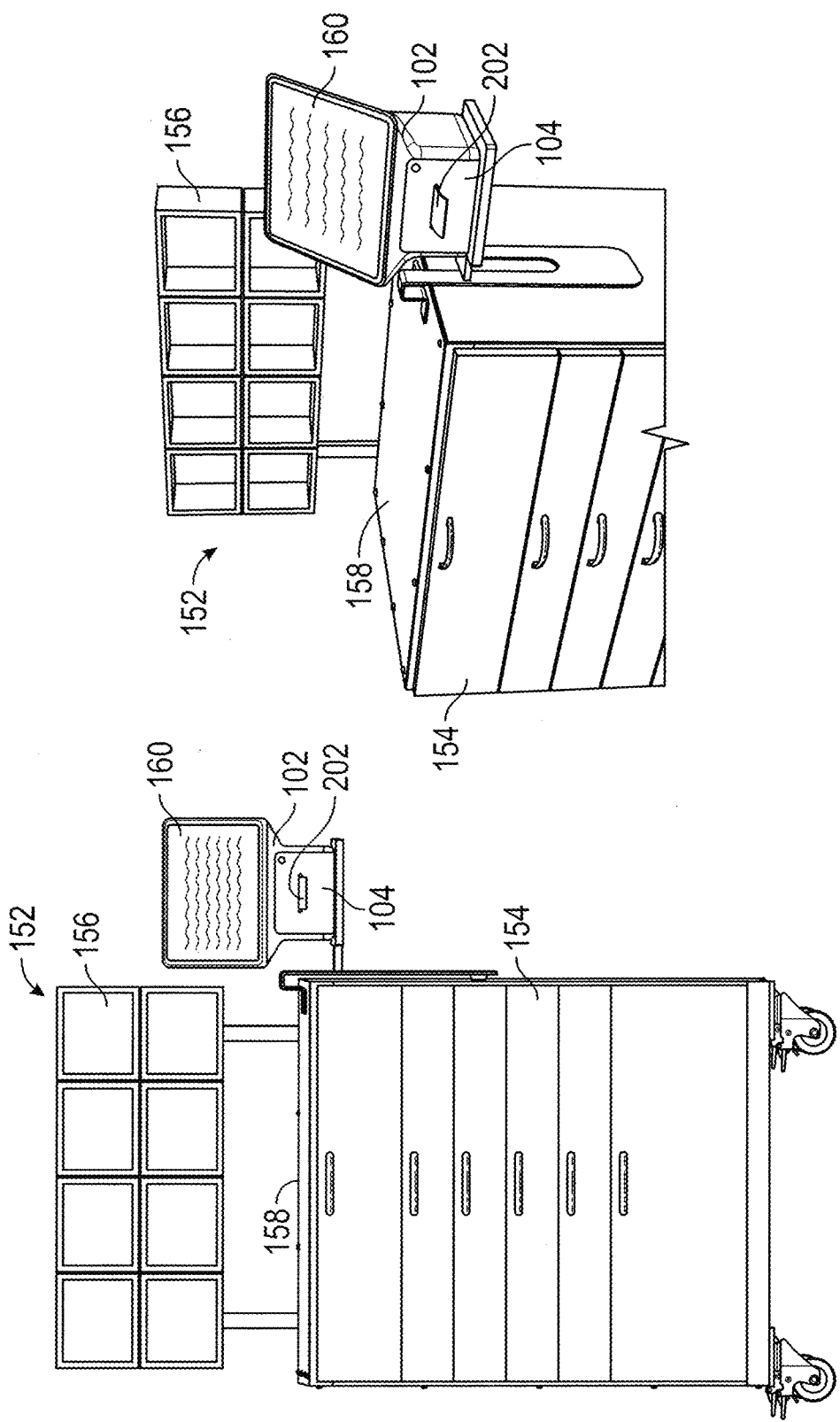
FIGS. 1B and 1C are diagrams illustrating an embodiment of a label reading station coupled to a pharmaceutical item storage unit.

FIGS. 1B and 1C are diagrams illustrating an embodiment of a label reading station 102 coupled to a pharmaceutical item storage unit 152, such as a crash cart. In the illustrated embodiment, the pharmaceutical item storage unit 152 includes drawers 154, shelves 156, and a tabletop 158. The drawers 154 can be locked drawers that require a key code to open. Within the drawers can be stored various medications, including, but not limited to drugs, diluents (for example, sterile water, sodium chloride, etc.), other supplies, etc. The shelves 156 can include unused medicinal containers and other medical supplies, such as tubes, baggies, gauze, etc., as desired. The tabletop 158 can be used for preparing the child medications and/or child medicinal containers. For example, the medications found in the drawers 154 can be combined or mixed together as part of the preparation for a new medication.

In the illustrated embodiment, the label reading station 102 includes a display 160, a label printer 104. In addition, the label reading station 102 can include a label reader (not shown), microprocessor, a data storage device, and a network interface. The microprocessor can be configured to execute instructions stored in the data storage device and to read and write data to and from the data storage device. The network interface can be used by the microprocessor to communicate with the electronic medical records database 110 and/or the information processing system 108, as described previously with respect to FIG. 1A.

The display 160 can be used to prompt a user for information and to display information regarding the medications, labels, patients, medicinal containers, etc. For example, the display 160 can be used to display a prompt for the user to tap a label to the display 160 or to move a label in close proximity to the display 160 such that the label reader 106 can read the label. In addition, the display 160 can be used to display information as the label reading station 102 prepares and prints a label. For example, the display 160 can display information regarding a medication that will be printed onto a new label.

The label reader 106 (not shown in FIGS. 1B and 1C) can be located behind the display 160 or in some other location within the label reading station 102, such that when a label touches or is placed in close proximity (for example, twelve inches or less, or some other desired distance) to the label reading station 102, the label reader 106 can read the contents of the label. Furthermore, in some embodiments, the label reader 106 can be configured to emit an electromagnetic field large enough to capture data from all RFID tags stored in the pharmaceutical item storage unit 152. In this way, the label reader 106 can determine when a medicinal container associated with an RFID tag is removed from the pharmaceutical item storage unit without having to touch the RFID tag, or place the RFID tag in close proximity, to the label reading station 102. Although described with respect to RFID technology, it will be understood that the labels can be implemented using any number or combination of technologies including, but not limited to bar codes, QR codes, etc.

As described previously with respect to FIG. 1A, the label reading station 102 can be used in conjunction with the information processing system 108 to verify the status of medications in the pharmaceutical item storage unit 152. For example, labels associated with or coupled to the medicinal containers in the pharmaceutical item storage unit 152 can be queried and read by the label reading station 102. Once read, the label reading station 102 can look up information regarding the medications, such as the expiration date, recall information, warnings, etc. The label reading station 102 can also be used to print labels for medicinal containers. The new labels may replace old labels on a medicinal container and/or can be placed on an unused or child medicinal container. The labels printed by the label reading station 102 will be described in greater detail below with reference to FIGS. 2A and 2B.

The label reading station 102 in conjunction with the information processing system 108 can further be used to manage inventory of the pharmaceutical item storage unit 152. For example, when a medication is removed from the pharmaceutical item storage unit 152 by a user and scanned by the label reading station 102, the information can be used to determine whether the pharmaceutical item storage unit 152 includes a threshold number of the medication that was removed. For example, if Propofol is removed from the pharmaceutical item storage unit 152 and there is only one vial of Propofol left in the pharmaceutical item storage unit 152, the label reading station 102 can generate a notification indicating that the pharmaceutical item storage unit 152 should be restocked with more Propofol.

In some embodiments, the label reading station 102 and/or information processing system 108 can track the total number of each medication found within the pharmaceutical item storage unit 152 and from use that information to determine whether a threshold has been satisfied. In some embodiments, the label reading station 102 and/or information processing system 108 can use a one out one in policy such that for each medication removed, the label reading station 102 and/or information processing system 108 can request a replacement medication.

In determining whether a threshold has been reached, the label reading station 102 and/or information processing system 108 can use templates, as described in greater detail in U.S. patent application Ser. Nos. 14/472,410, and 13/554, 342, each of which is incorporated herein by reference in its entirety. The templates can be used to identify substitute medications that can be used when a particular medication is not present. For example, the templates can indicate a generic version of a branded drug and/or other drugs that can be used as a substitute. In some embodiments, the substitute drug can be the same drug but at a different concentration or a different amount. In certain embodiments, the substitute drug may not be chemically equivalent and/or have a different active ingredient, but is deemed medically suitable for a particular use or as a substitute to the missing drug.

The label reading station 102 and/or information processing system 108 can further be used to manage and track which medications are in a user's possession. For example, when a doctor scans a label for medication A, medication A can be associated with the doctor, indicating that the doctor is in possession of a particular medicinal container storing medication A. Accordingly, throughout the day, as the doctor removes medications from pharmaceutical item storage units 152, administers medications to a patient, or wastes medications, the label reading station 102 and/or information processing system 108 can be used to track all of the medications in the doctor's possession. This information can be used by the pharmacy to reconcile all medications used by the doctor and ensure medications are not misplaced, lost, or abused.

The label reading station 102 and/or information processing system 108 can further be used to handle and reconcile waste. For example, after a doctor has administered a medication to a patient, any remaining portions of the medication in a vial or syringe may need to be discarded. Accordingly, the label reading station 102 and/or information processing system 108 can provide prompts for the doctor to discard the medications, and in some embodiments, prompt a second doctor to act as a witness for the reconciliation or waste of the medication.

In the illustrated embodiments of FIGS. 1B and 1C, the label reading station 102 is coupled to the pharmaceutical item storage unit 152. However, it will be understood that the label reading station 102 can be located in any one or more locations within a medical care facility. For example, the label reading station 102 can be located in an operating room, in a patient room, or in a pharmacy. Furthermore, the label reading station 102 can be used in conjunction with the information processing system 108 to track the administration of medications to a patient, determine allergic reactions of the medication with a particular patient, update an electronic medical record of a patient, calculate waste based on an amount of medication given to a patient, and/or determine whether a particular medication has been used previously, such as on a different patient, or is expired or recalled.

As a non-limiting example, when a doctor enters a patient's room and/or an operating room in which medications will be administered to a patient, the label reading station 102 can scan or read the contents of an RFID tag associated with a particular medication. In this situation, the medication can be associated with the patient that is in the patient room or operating room. Using this information, the label reading station 102 and/or information processing system 108 can determine whether the patient may have any allergic reactions to the medication, update the patient's electronic medical record with information regarding the administration of the medication, and/or calculate the waste based on the amount of the medication used on the patient. In addition, the label reading station 102 and/or information processing system 108 can determine whether the medication or medicinal container has been used previously. In this manner, the label reading station 102 and/or information processing system 108 can prevent multiple uses of a medicinal container, such as a syringe, on different patients.

In some embodiments, the label reading station 102, can omit the display 160 and/or the label printer 104. Furthermore, the label reading station 102 can be any form factor, including a smaller or more portable electronic device, such as a phone, tablet, personal electronic device, etc. For example, a smaller or more portable form factor of the label reading station 102 can be used in an operating room and/or a patient's room to conserve space.

Furthermore, in some embodiments, a smaller form factor of the label reading station 102 can be used as a type of wand to inventory the contents of the pharmaceutical item storage unit 152. Once the contents of the pharmaceutical item storage unit 152 are inventoried, the information processing system 108 can generate a template for the pharmaceutical item storage unit 152 for restocking purposes and/or compare the inventoried items with a template to determine whether any items are to be restocked.

Labels

Figure 2A:
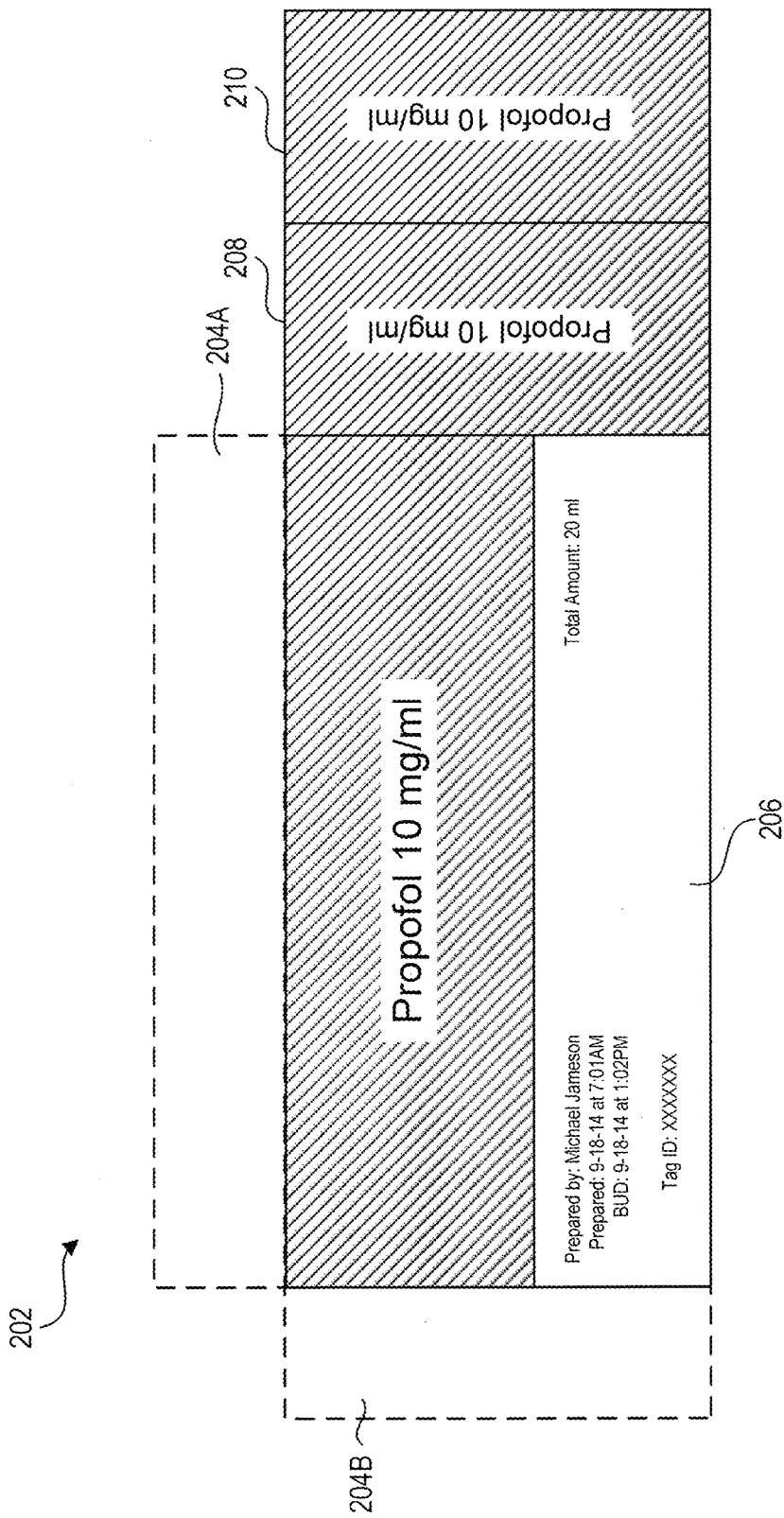
FIGS. 2A and 2B are diagrams illustrating embodiments of a drug label.
Figure 2B:
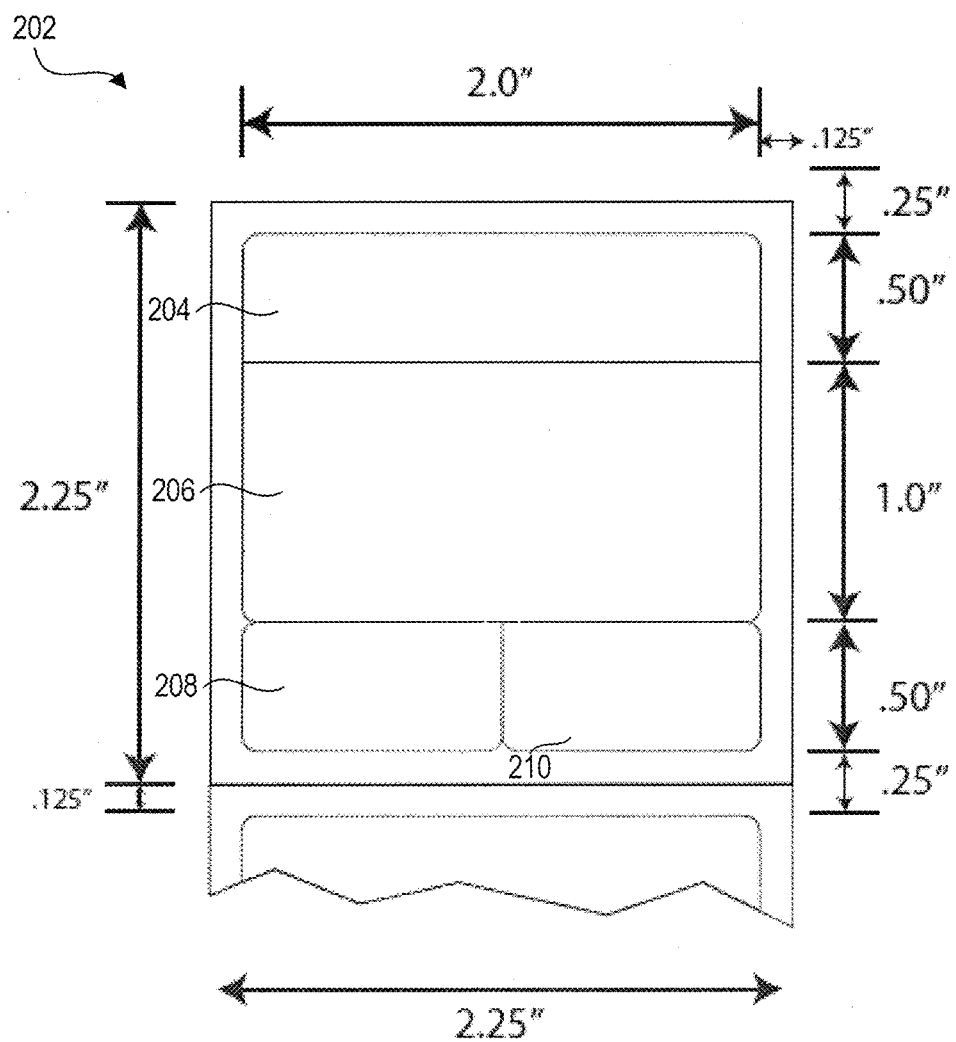

FIGS. 2A and 2B are diagrams illustrating embodiments of a label 202 that can be printed by the label printer 104. In the illustrated embodiments of FIGS. 2A and 2B, the label 202 includes an applicator portion 204 (204A and/or 204B), an RFID portion 206, and abbreviated data portions 208, 210. The applicator portion can stand lengthwise across a longitudinal portion of the RFID portion 206 (for example as is shown with portion 204A in FIG. 2A or applicator portion 204 in FIG. 2B), or can extend height-wise along a latitudinal portion of the RFID portion 206, as shown with applicator portion 204B.

Similarly, the abbreviated data portions 208, 210 can extend height-wise along a latitudinal portion of the RFID portion 206, as is shown in FIG. 2A, or lengthwise along a longitudinal portion of the RFID portion 206, as is shown in FIG. 2B. In addition, the abbreviated data portions 208, 210 can share or be coupled with each other along a longitudinal portion, as is shown in FIG. 2A, or along a latitudinal portion, as is shown in FIG. 2B.

In the illustrated embodiment of FIG. 2A, text printed on the RFID portion 206 is oriented at a 90° angled difference from the text printed onto the abbreviated data portions 208, 210. In the illustrated embodiment of FIG. 2B, the text printed on the RFID portion 206 can have the same orientation as text printed onto the abbreviated data portions 208, 210.

Although FIGS. 2A and 2B illustrate specific embodiments of the label 202, it will be understood that the various portions can be coupled together in a variety of orientations as desired. Furthermore, text printed on any one or more of the portions can be printed in the same orientation or in different orientations, as desired. In addition, although in the illustrated embodiments, the applicator portion 204 extends across an entire length or height of the label, it will be understood that it can extend along a more or less of the RFID portion 206 as desired. For example, the applicator portion 204A can extend along less than the entire length of the RFID portion or more than the length of the RFID portion 206. Similarly the applicator portion 204B can extend along the less than the entire height of the RFID portion 206 or more than the entire height of the RFID portion 206. In some embodiments, the abbreviated data portions 208, 210 can be detachably coupled to the RFID portion 206 and/or to each other. In this way, the abbreviated data portions 208,210 can be removed from the rest of the label 202 and applied to different portions of a medicinal container in order to provide a user the ability to read information regarding the contents of the medicinal container from a variety of positions, angles, or orientations.

The applicator portion 204 can include an adhesive formed on one side and can be transparent or translucent. In this way, the applicator portion 204 can be applied to a medicinal container, such as a syringe, without obscuring the view of any information printed on the medicinal container, such as units of measure. However, it will be understood that the applicator portion 204 can be opaque.

In embodiments where the applicator portion 204 extends lengthwise across a longitudinal portion of the RFID portion 206, the label 202 can be applied to the medicinal container in such a way as to reduce the amount of the label that extends away from the medicinal container. This can reduce the likelihood of the label 202 catching onto some other object.

In certain embodiments in which the applicator portion 204 (for example, applicator portion 204B) in which the applicator portion 204 extends along a latitudinal portion of the RFID portion 206, the label 202 can be configured so as to minimize or reduce the amount of adhesive used in coupling the label 202 to the medicinal container.

In the illustrated embodiment, the RFID portion 206 includes an RFID tag, a printable surface, and is opaque. However, it will be understood that the RFID portion 206 can use other machine-readable data, such as a bar code or QR code, etc. In addition, it will be understood that in some embodiments, the RFID portion can be transparent or translucent and/or not include a printable surface. Furthermore, in some embodiments, the RFID portion 206 does not include an adhesive, and in certain embodiments, the RFID portion includes an adhesive.

The RFID portion 206 can include machine-readable data, as well as human-readable text. The machine-readable data can include a serialized identifier or unique ID stored on an RFID tag, which distinguishes the RFID tag from other RFID tags that are registered with the information processing system 108. In this way, the information processing system 108 can store data that is unique to the label 202, and enables the information processing system 108 to distinguish the label and the medicinal container to which the label is attached from all other medicinal containers, including medicinal containers that form part of the same lot as the medicinal container.

Using the unique identifier, the information processing system 108 can store and look up data unique to the label 202. For example, the data can include one or more lot numbers to which the medication or medicinal container belongs, chain of custody data, expiration data, recall data, drug class data, concentration data, total medication amount data, preparation data, transfer data, etc. This data can be used by the information processing system 108 to verify the status of the medication contained within the medicinal container, produce warnings, provide instructions and/or information, and print labels. In some embodiments, the RFID portion 206 can store some or all of the data on the RFID tag included within the RFID portion 206. In some embodiments, the RFID tag included within the RFID portion 206 includes only the unique identifier, and the other data associated with unique identifier is stored at the label reading station 102 and/or the data storage device 114 of the information processing system 108.

In addition to the RFID tag, the RFID portion 206 can include text, and other information regarding the medication and/or the medicinal container to which the label 202 is affixed. For example, the RFID portion 206 can include a color identifier identifying the drug class of the medication, a drug name, concentration of the drug, total amount of the drug, expiration data, user identifier, preparation data, and/or any other information desired. In this way, a user can read the text on the RFID portion 206 to determine the contents of the medicinal container. As mentioned previously, although reference is made to an RFID tag forming part of the RFID portion 206, it will be understood that other machine-readable identifiers can be used, such as, a bar code, QR code, etc. Such identifiers can include either a unique identifier or serialized identifier, or additional data as described previously.

The abbreviated data portions 208, 210 in the illustrated embodiment of FIG. 2A are opaque and include some of the data printed on the RFID portion 206. For example, the abbreviated data portions 208, 210 of FIG. 2A include the drug name and the concentration, as well as a color code identifier indicating the class of the drug. However, it will be understood that the abbreviated data portions 208, 210 can be transparent and/or translucent and need not have an adhesive portion. Furthermore, as mentioned previously the abbreviated data portions 208, 210 can be detachably coupled to the RFID portion 206, such as using a perforated line, a separate sheet, etc. such that the abbreviated data portions 208, 210 can be removed separately from the RFID portion 206 and affixed to different portions of the medicinal container, as desired.

Furthermore although illustrated as having two abbreviated data portions 208, 210, it will be understood that the label 202 can have fewer or more abbreviated data portions as desired. For example in some embodiments, the label 202 does not include any abbreviated data portions or only one abbreviated data portion. In certain embodiments, the label 202 can include three or more abbreviated data portions arranged in any number of orientations, such as the orientation shown in FIG. 2A or 2B, or any other orientation as desired.

With respect to FIG. 2B, specific lengths and heights of the label 202, the applicator portion 204, the RFID portion 206, and the abbreviated data portions 208, 210 are provided. However, it will be understood that the label 202, the applicator portion 204, the RFID portion 206, and the abbreviated data portions 208, 210 can be configured using any dimension as desired. Accordingly, the dimensions illustrated in FIG. 2B should not be construed as limiting.

Mixing and Dilution

Figure 3A:
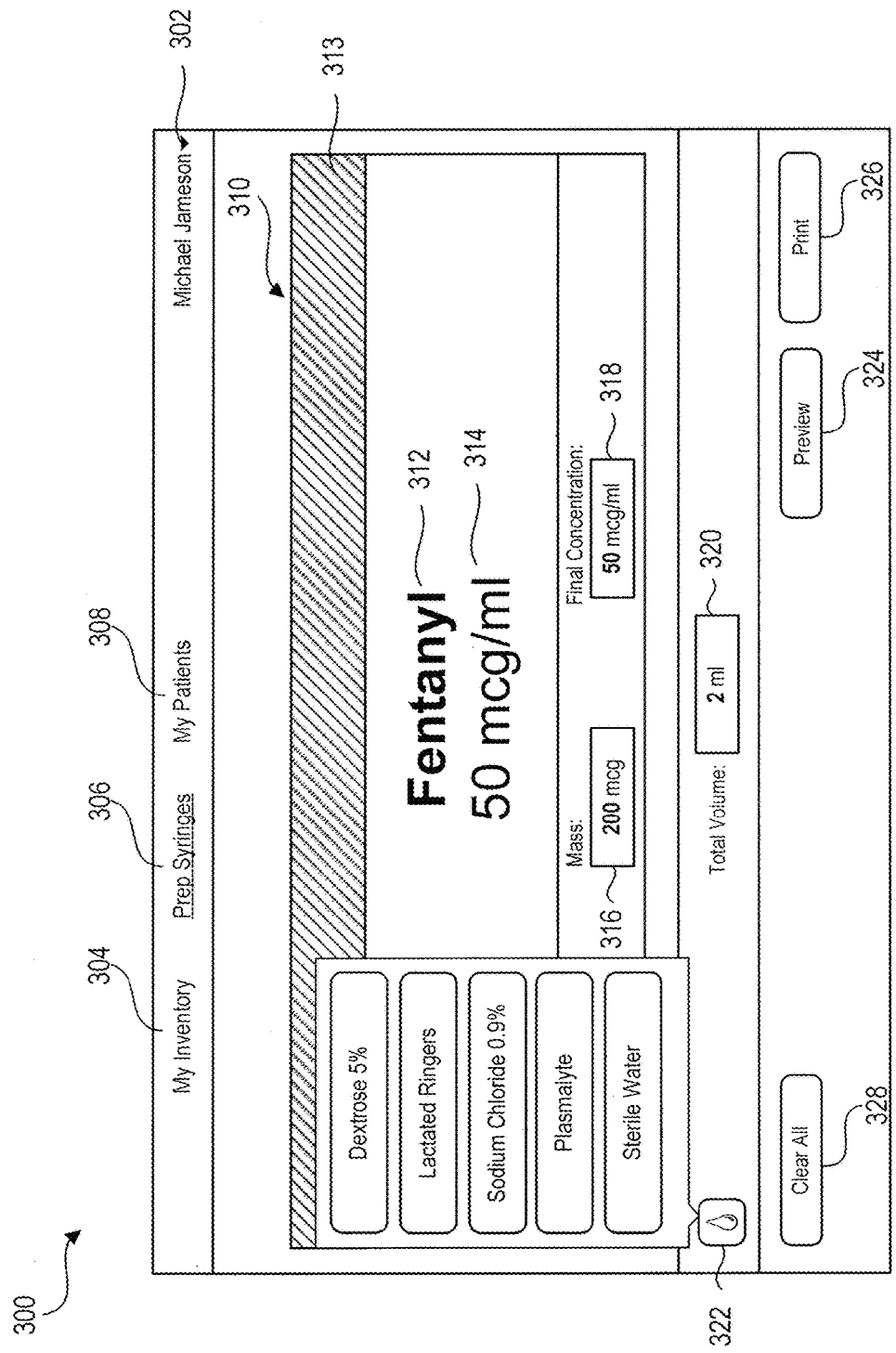
FIGS. 3A and 3B depict embodiments of a user interface for mixing and/or diluting one or more medications.
Figure 3B:
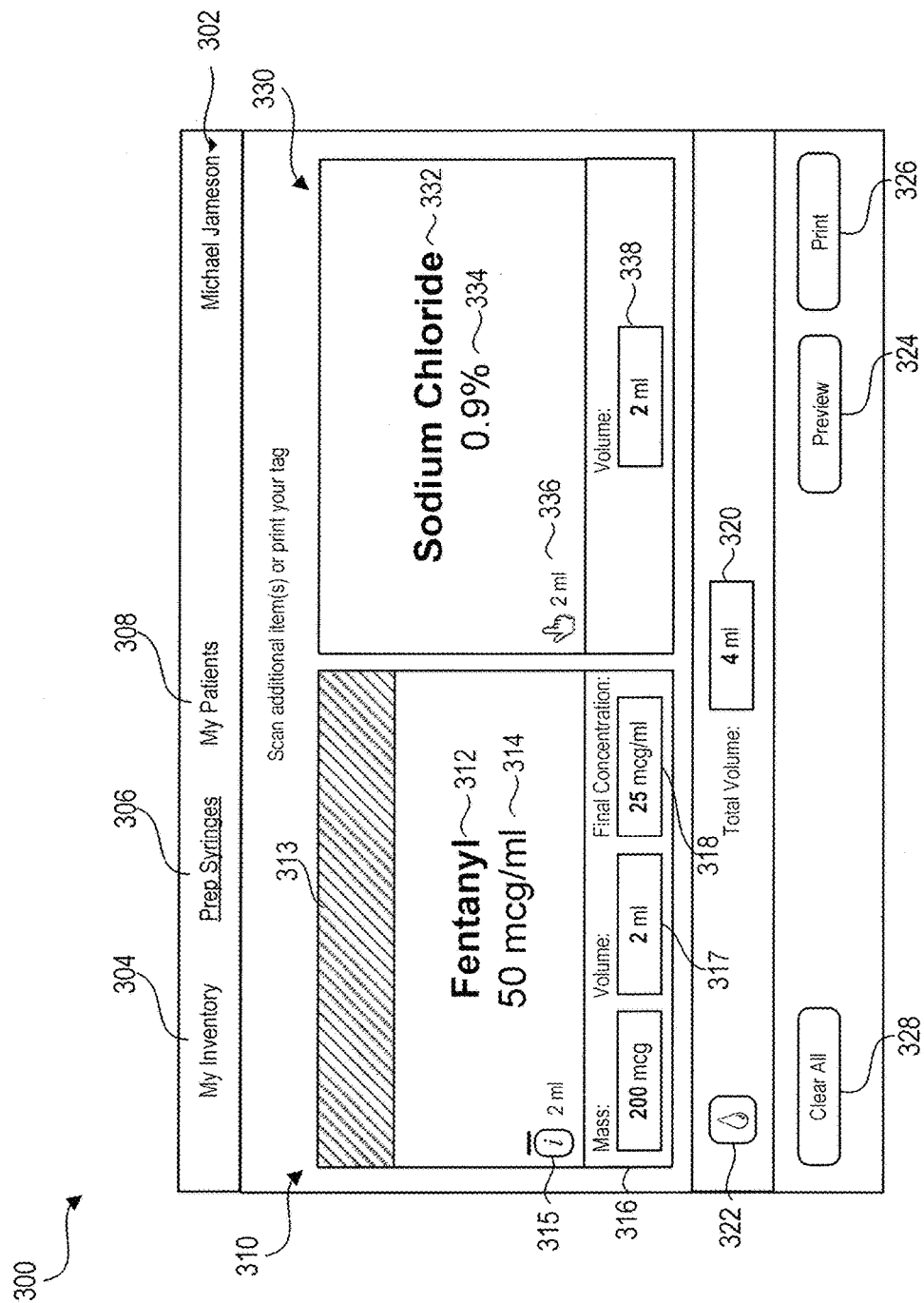

FIGS. 3A and 3B depict embodiments of a user interface 300 for mixing and/or diluting a medication. In some embodiments, the user interface 300 can be presented on the display 160 of the label reading station 102 after a label 202 has been read by the label reading station 102.

FIG. 3A depicts an embodiment in which one label 202 has been read and FIG. 3B depicts an embodiment of the user interface 300 in which two labels 202 have been read by a label reading station 102. It will be understood that additional labels 202 can be read as desired and/or medication information can be entered manually.

In the illustrated embodiments of FIGS. 3A and 3B, the user interface includes user data 302, an inventory link 304, a medicinal container preparation link 306, and a patient data link 308, first medication information 310, second medication information 330 (FIG. 3B), a total volume field 320, a mixture object 322 and other interface objects, including a preview object 324, a print object 326, and a clear all object 328.

The various links 304, 306, 308 can be used to navigate to various portions of the user interface 300. For example, the inventory data link 304 can be used to navigate to a portion of the user interface 300 displaying medications that are in the possession of a user, as well as additional information regarding the use of those medications, such as the embodiments of the user interface 300 illustrated in FIGS. 4 and 6. The medicinal container preparation link 306 can be used to navigate to portions of the user interface 300 for preparing labels 202 for medicinal containers, such as the embodiments illustrated in FIGS. 3A and 3B. The labels 202 can be prepared for medicinal containers that already include a label 202 and/or can be prepared for medicinal containers that do not include a label 202. The patient data link 308 can be used to navigate to portions of the user interface in which data regarding individual patients associated with the user are displayed, such as the embodiments of the user interface 300 illustrated in FIGS. 5A, 5B, and 5C.

The medication names 312, 332 can include a proper name for the medication, a generic name for the medication and/or other identifying name for the medication. The class identifier 313 can indicate the class of the medication, such as a drug classification. In some embodiments, the class identifier can be a color coded drug class identifier, or other identifier to indicate the classification of the medication or drug.

The mass field 316 can indicate the total mass of the medicinal container associated with the label 202 that is scanned by the label reading station 102. The final concentration field 318 can indicate the final concentration of the child medication or content of a child medicinal container. The total volume field 320 can indicate the total volume of the child medication or content of the child medicinal container.

The first medication volume field 317 can indicate the volume of the parent medication being removed or the volume being removed from the parent medicinal container. Similarly, the second medication volume field 338 can indicate the volume of the parent medication being removed and/or the volume being removed from the second parent medicinal container and being added to the child medicinal container to form the child medication.

By interacting with the mixture object 322, the system can provide the user with one or more suggestions of diluents that can be combined with the medication 312, as illustrated on FIG. 3A. The suggested medications can be based on medical facility rules (for example, medications that the medical care facility has indicated as being permissibly combined with a particular medication), best practices, user preferences (for example, medications that the user has indicated that they prefer to use with a particular medication), and/or user history (for example, previous medications that the user has used in the past).

The additional interface objects 324, 326, 328 can be used to control portions of the user interface 300 and/or navigate to different portions of the user interface 300. For example, interacting with the preview object 324 can provide the user with a preview of a label to be printed based on the contents of the user interface 300, and interacting with the print object 326 can cause the label reading station 102 to print a label 202 based on the information displayed on the user interface 300.

With continued reference to FIGS. 3A and 3B, once the relevant information has been captured regarding the generation of a new label, the label reading station 102 can communicate the information to the information processing system 108. In response, the information processing system 108 can generate a new database entry in the data storage device 114 for the child medication or child medicinal container. The new database entry can include information regarding the drug name, class identification, concentration, origin information (including information regarding the parent medications or parent medicinal containers), expiration, volume information, lot number information regarding the parent medications or parent medicinal containers, and other information to track the child medication or child medicinal container.

Once the new label 202 is printed, the unique identifier from the RFID tag of the label 202 can be associated with the new database entry. In some embodiments this association can take place during the printing of the label 202 and/or following the printing of the label 202. For example, a user can tap or place the newly generated label 202 on or near the label reading station 102. The label reading station 102 can read the unique identifier from the label 202 and use that information to associate the unique identifier with the data regarding the contents of the new medicinal container.

In addition, as part of this process, the information processing system 108 can update the medication data associated with the parent medications or parent medicinal containers. For example, the information processing system 108 can update an expiration date for the parent medications or parent medicinal containers from a sealed expiration date to a broken seal expiration date, a vial expiration date to a syringe expiration date, and/or a refrigerated expiration date to a non-refrigerated expiration date, etc., as described in greater detail below.

In some embodiments, the information processing system 108 can reduce quantity data associated with the parent medications or parent medicinal containers and increase quantity data associated with the child medication or child medicinal container. For example, if the parent medicinal container is a vial and included four mL of Fentanyl, two of which were removed and placed into the child medicinal container to form the child medication, the information processing system 108 can decrement the quantity data associated with the parent medication and/or parent medicinal container by two mL and increase the child medication or contents of the child medicinal container by two mL.

The first medication information 310 can include, but is not limited to, a medication name 312, a class identifier 313, concentration data 314, a mass field 316, a final concentration field 318, origin data 315 indicating the origin of the medication (shown in FIG. 3B), and a first medication volume field 317 (shown in FIG. 3B).

The second medication information 330 can include similar information. In the illustrated embodiment of FIG. 3B, the second medication information 330 includes a medication name 332, concentration data 334, origin data 336 indicating the origin of the second medication, and a second medication volume field 338. It will be understood that the medication information for each medication can include less or more information as desired.

The various fields illustrated in the user interface 300 can be fillable fields or auto populated. In some embodiments some of the fields auto populate based on data collected in a fillable field. For example, the total volume field 320 can auto populate based on the contents of the first medication volume field 317 and the second medication volume field 338. Similarly, the final concentration field 318 can also be auto populated based on the information from the mass field 316, the first medication volume field 317, and/or the second medication volume field 338.

The origin data 315, 336 can indicate the origin of the medications, respectively. For example, the origin data 315 can indicate that the first medication originated from a medicinal container such as a vial that also includes a label 202 uniquely identifying the vial. The origin data 336 can indicate that the second medication originates from a medicinal container that does not include a label 202. For example, the second medication can originate from an IV bag or drip line that is not tracked and/or does not include a label 202.

Medical Care Provider Inventory

FIG. 4 depicts an embodiment of the user interface 300 for monitoring medications that are in the custody or care of a particular medical care provider. In the illustrated embodiment of FIG. 4, the particular medical care provider is "Michael Jamison," as indicated by the user data 302. In the illustrated embodiment of FIG. 4, the user interface provides data regarding the medications that are in the care of the medical care provider, the amount of each medication, and indications regarding a quantity of each medication that needs to be returned to the pharmacy or accounted for.

In the illustrated embodiment of FIG. 4, the user interface provides the medication name and concentration 402, a medication volume 404, and a quantity of medicinal containers of the particular medication 406. As the medical care provider uses, wastes, or returns the medicinal containers, the information processing system 108 can update the inventory data of the user. In this way, the information processing system 108 can maintain an accurate record of the medications in the custody of the medical care providers in a particular medical care facility.

Medication Administration

Figure 5A:
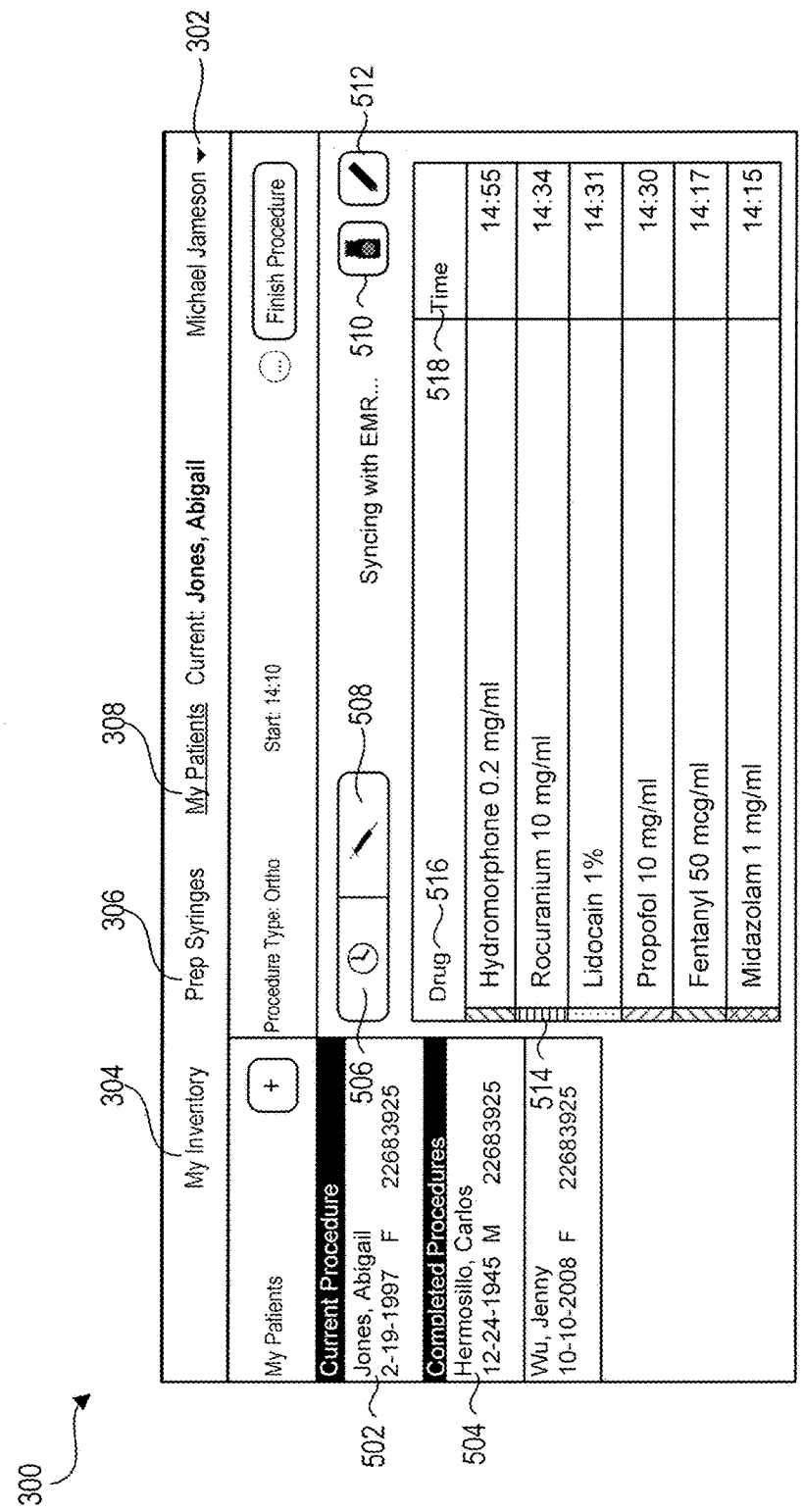
Figure 5C:
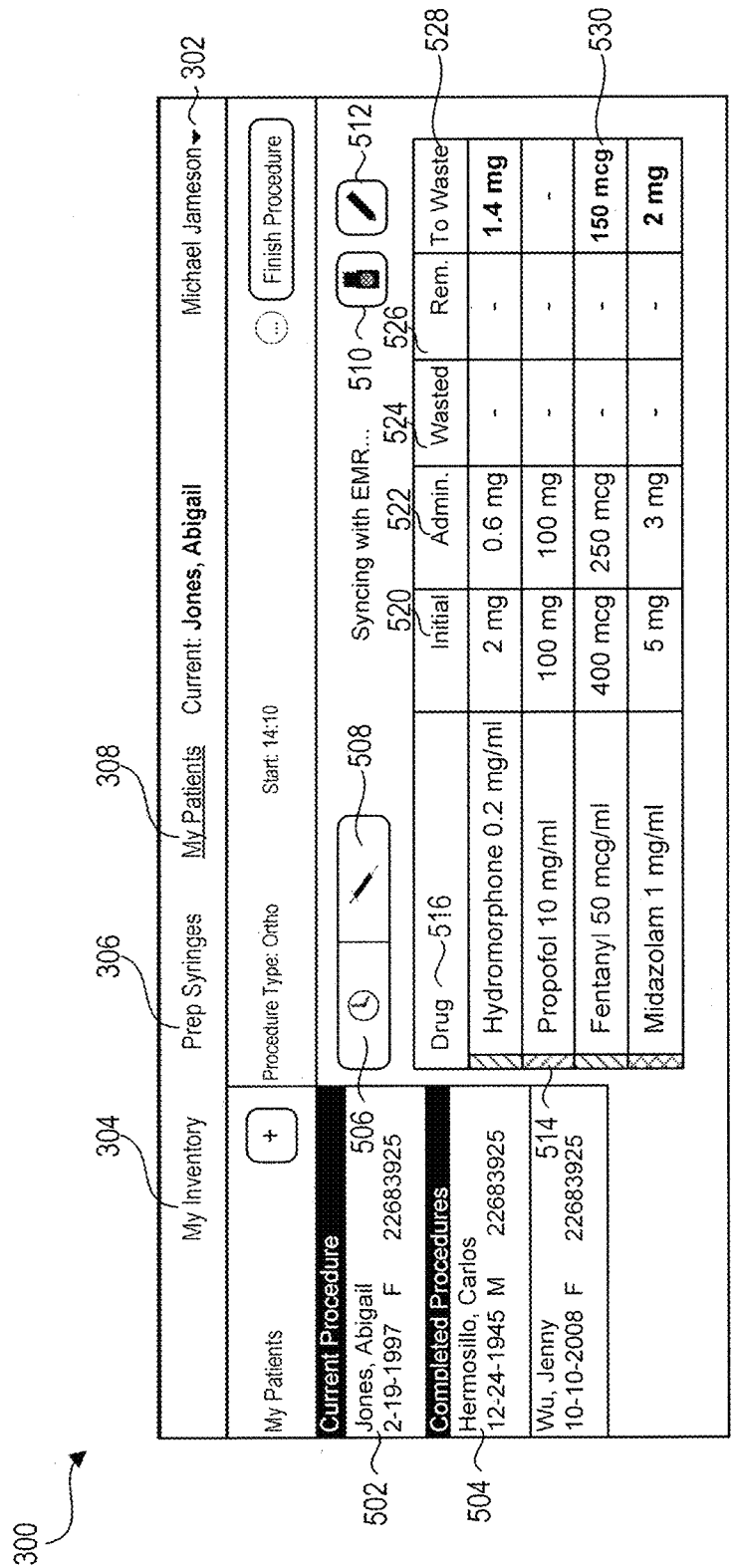

FIGS. 5A, 5B, and 5C depict embodiments of the user interface 300 for monitoring the administration of medications for a particular patient. In some embodiments, the user interface 300 of FIGS. 5A, 5B, and 5C can be presented on the display 160 of the label reading station 102 once a user logs into a label reading station 102 located in a patient administration environment, such as an operating room or patient room, and indicates that medications are to be provided to a particular patient.

In some embodiments, the information processing system 108 can automatically determine that medications are to be provided to a particular patient based at least in part on the location of the label reading station 102 and the electronic medical records of the particular patient. For example, if the label reading station 102 is located in operating room 1 and the medical records of Abigail Jones indicate that she is in operating room 1, when the medical care provider logs into or accesses the label reading station 102, the information processing system 108 can automatically determine that a procedure is in progress for Abigail Jones and that the medical care provider will be administering medications to Abigail Jones.

As the label reading station 102 in the operating room 1 reads RFID tags associated with various medicinal containers, the information processing system 108 can associate the various medicinal containers with the Abigail Jones and with the medical care provider (if it has not already done so as part of a label creation). As the RFID tags are scanned, information regarding them can be displayed on the user interface 300. Furthermore, the information processing system 108 can verify the status of the medications, log the date and time of administration, determine whether Abigail Jones may have any allergic reactions to the medications, etc. The label reading station 102 can display applicable warnings based on the processing of the information processing system 108. For example, the label reading station 102 can display or sound a warning indicating a possible allergic reaction to a medication, an adverse reaction between two medications, an expired medication, etc.

As the medications are administered, the information processing system 108 can update the data storage device 114, personal health data storage device 116 and/or the electronic medical records database 110. For example, the information processing system 108 can indicate in the personal health data storage device 116 and/or the electronic medical records database 110 that a particular medication has been administered to the patient.

In addition, the information processing system 108 can update the medication data for the particular medication to indicate the quantity that was administered. From that information, the information processing system 108 can determine the amount of the medication that is to be returned or wasted. Furthermore, the information processing system 108 can update any expiration dates associated with the medication. For example, the expiration date may be changed from a sealed expiration date to a broken seal expiration date, as described in greater detail below.

In the illustrated embodiments of FIGS. 5A, 5B, and 5C, the user interface 300 includes a current patient data 502, completed procedure patient data 504, a medication delivery time icon 506, a medication detailed information icon 508, add/edit medication icons 510, 512, and information regarding medications used during the procedure, including drug classification 514, medication name/concentration data 516, time of administration 518.

The patient data 502 and completed procedure patient data 504 can include information uniquely identifying a patient, such as a patient name, date of birth, gender, and/or a patient identification number, etc. The patient data 502 and completed procedure patient data 504 can correspond to patients with whom the user or medical care provider is working or has worked. As mentioned previously, the label reading station 102 and/or information processing system 108 can communicate with an electronic medical records database 110 to retrieve data regarding the patients of a particular medical care facility. Using the data from the electronic medical records database 110, the information processing system 108 can associate the patients with a particular medical care provider.

The medication delivery time icon 506 and medication detailed information icon 508 can be used to alter the information displayed on the user interface 300. In the illustrated embodiment of FIG. 5A, the medication delivery time icon 506 is selected and in the illustrated embodiment of FIG. 5B, the medication detailed information icon 508 is selected.

The add/edit medication icons 510,512 can be used to add information regarding additional medications that are used during the current procedure with the identified patient. In some embodiments, the information can be added by scanning an RFID tag associated with a medicinal container.

The medication name/concentration data 516 can be similar to the drug name/concentration data 402 described previously with respect to FIG. 4. The time of administration 518 can indicate the time at which a particular medication is administered to the patient. The drug classification 514 can indicate the classification of the medication or drug that is administered to the patient, as described previously.

The user interface can include additional information and objects as desired. For example, in the illustrated embodiment of FIGS. 5A, 5B, and 5C, the user interface 300 includes information regarding the type of procedure being performed on the patient, the start time of the procedure, and a finish procedure object to indicate when the procedure for the patient is completed and/or when the medical care provider leaves the procedure.

As mentioned previously, FIG. 5B includes an illustrated embodiment of the user interface 300 when the medication detailed information icon 508 is selected. Accordingly, in the illustrated embodiment of FIG. 5B, the user interface 300 further includes initial amount data 520, administered amount data 522, wasted amount data 524, remainder amount data 526, and to waste amount data 528 for each medication.

In the illustrated embodiment, it is shown that a vial containing five milligrams of Midazolam was associated with the patient. Of the five milligrams, three milligrams were administered to the patient. Accordingly, the to waste amount data 528 of the user interface 300 indicates that two milligrams of Midazolam are to be wasted. Once wasted, the user interface 300 can be updated to reflect the wasted amount 524 as 2 mg and the to be wasted amount 528 as zero.

Furthermore, in the illustrated embodiment of FIG. 5B, a vial containing 200 micrograms of Fentanyl has been associated with the patient, Abigail Jones. However, the illustrated embodiment indicates that 250 micrograms of Fentanyl were administered. In such an instance when the amount administered exceeds the initial amount of the medicinal container, a warning icon 530 can be provided. In addition, a warning message or popup window can be displayed requesting additional information regarding the discrepancy between the initial amount of the medication and the amount administered. Using the popup window or additional data field, a user can provide information indicating an additional initial amount 520. For example, it may be that the medical care provider used a second medicinal container and administered 50 micrograms of Fentanyl from the second medicinal container without the label reading station 102 scanning an RFID tag associated with the second medicinal container. Accordingly, the medical care provider can update the initial amount of Fentanyl from 200 micrograms to 400 micrograms by scanning the RFID tag associated with the second medicinal container (or manually entering the information). Upon updating the information, the information processing system 108 can calculate that the amount of Fentanyl to be wasted is 150 micrograms and the user interface 300 can be updated accordingly, as illustrated in FIG. 5C.

Medication Reconciliation

FIG. 6 depicts an embodiment of a user interface 300 for reconciling/wasting medications. In the illustrated embodiment of FIG. 6, the user interface 300 includes medication summary data 602, to waste medication quantity 604, and to return medication quantity 606. The medication summary data 602 can include a list of medications that are in the possession of the medical care provider or user.

The to waste medication quantity 604 can include the number of medicinal containers that include medications that are to be wasted. In the illustrated embodiment of FIG. 6, there are four medicinal containers that include medications that are to be wasted.

The to return medication quantity 606 can indicate the number of medicinal containers that are to be returned to the pharmacy. This quantity may indicate medicinal containers that were never used by the medical care provider or medicinal containers that include medications that can be reused by the pharmacy.

In addition, the user interface 300 can include additional information regarding the medications that are to be wasted. For example, the user interface 300 can include medication data 608, initial quantity data 610, to waste quantity data 612, and drug classification data 614. As described in greater detail above, the item data 608 can include medication name and concentration, the initial quantity data 610 can include an initial quantity of a medication and a particular medicinal container, the to waste quantity data 612 can indicate the total amount of the particular medication that is to be wasted, and a drug classification data 614 can indicate a drug classification of the particular medication.

For medications that are to be returned, the user interface 300 can include some or different information as the information that is used for the medication that is to be wasted. For example, the user interface 300 can indicate item data 608, medicinal container volume data 616, quantity of medicinal containers to return data 618, and drug classification data 614.

The medicinal container volume data 616 can include information regarding the volume of the medication within a particular medicinal container and the quantity of medicinal containers to return data 618 can indicate the number of medicinal containers containing a particular medication that are to be returned to the pharmacy.

In addition, the user interface 300 can include a to waste witness icon 620. By interacting with the waste witness icon 620, the user interface 300 can enable the user to waste the medications. The user interface can control what the user is able to do in order to enforce one or more policies set by the medical care facility. For example, the user interface can require another medical care provider to witness the wasting of the medications. In addition, the user interface can require the witness to sign and/or scan in in order to ensure that the witness is present for the wasting.

Following the wasting and reconciliation of the medications, the information processing system 108 can generate a receipt indicating the inventory of the medications that were in the possession of the user, as well as a detailed report regarding which medications were administered to which patients, which medications were wasted (and their quantity), the identification of the witness, and which medications were returned to the pharmacy, etc. In this regard, the information processing system 108 can provide a complete audit trail and chain of custody of a medication throughout its use at a medical care facility.

Flow Diagrams

Figure 7:
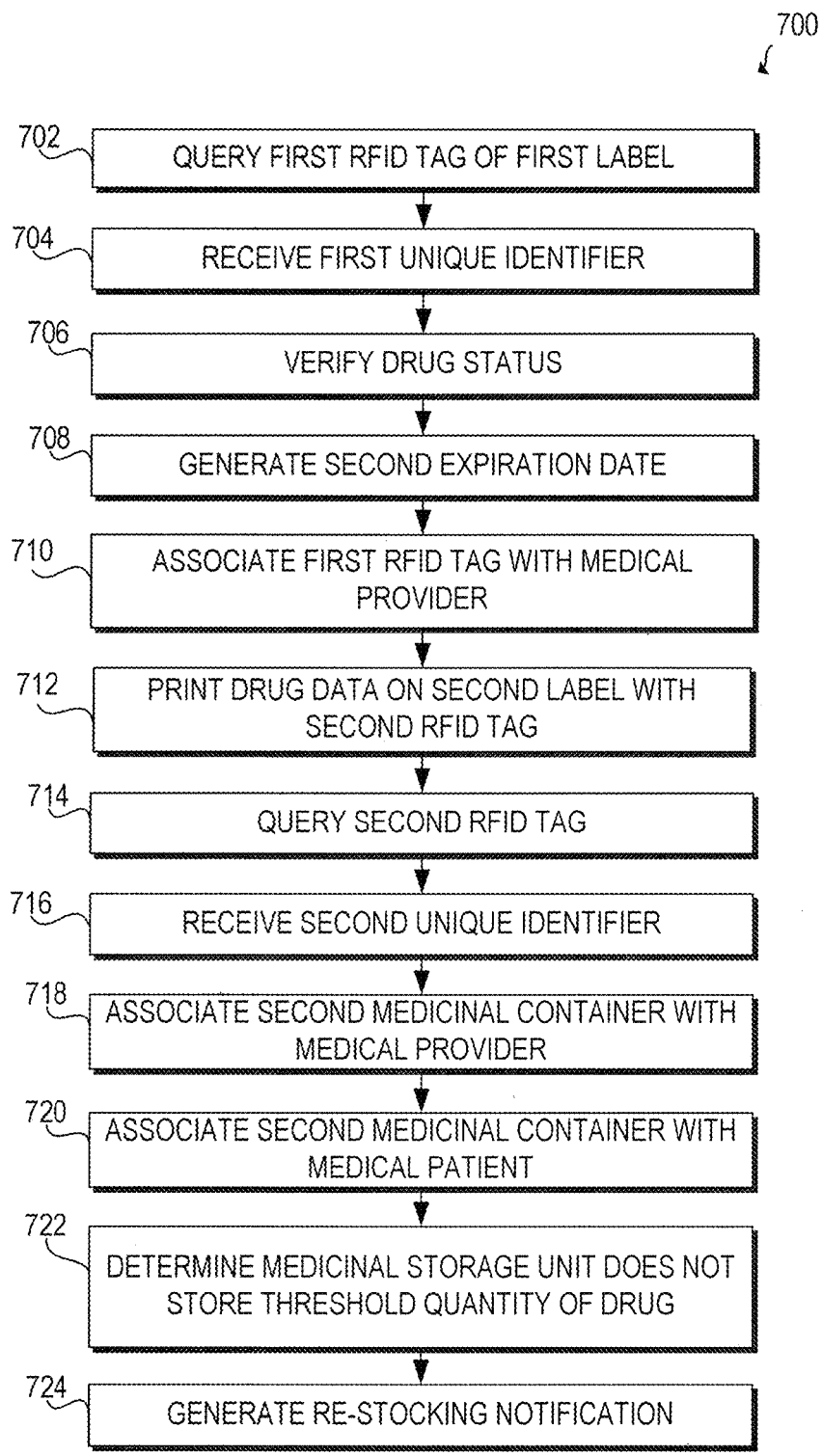
FIG. 7 is a flow diagram illustrating an embodiment for generating a label during a transfer of a drug and generating a restocking notification.

FIG. 7 is a flow diagram illustrating an embodiment of a routine 700 for generating a label during a transfer of a medication, and generating a restocking notification. In some embodiments, routine 700 can be used when a medical care provider desires to transfer one or more medications from one or more parent medicinal containers to a child medicinal container, or create a child medication from one or more parent medications.

One skilled in the relevant art will appreciate that the elements outlined for routine 700 can be implemented by one or many computing devices/components that are associated with the environment 100, including, but not limited to, the label reading station 102, the information processing system 108, and/or the electronic medical records database 110, or any combination thereof. For simplicity, routine 700 has been associated as being generally performed by the label reading station 102, and thus the following illustrative embodiments should not be construed as limiting.

At block 702, the label reading station 102 queries a first RFID tag of a first label. To query the first RFID tag, the label reading station 102 can emit an electromagnetic wave that activates the first RFID tag or causes the RFID tag to emit a response. In some embodiments, such as when an RFID tag is not used, the label reading station 102 can include a QR code reader or bar code reader that is able to query the first label containing machine-readable data.

At block 704, the label reading station 102 receives a first unique identifier from the first label. As mentioned previously, each RFID tag can include a unique identifier that uniquely identifies that RFID tag from all other RFID tags in a particular pharmaceutical item storage unit, at the medical care facility and/or that are tracked by the information processing system 108. In this way each medicinal container associated with an RFID tag can be uniquely identified.

Furthermore the information processing system 108 can include a database entry for each unique identifier. The database entry for the unique identifier can include information regarding the medicinal container, medication name, drug classification, concentration of the medication within the medicinal container, total volume, lot numbers associated with the medication and/or the medicinal container, expiration data of the medication, recall information regarding the medication, national drug code (NDC), user and facility audit information, multi-dose information, refrigerated information, and/or event history etc. In some embodiments, the RFID tag can store some or all of the data associated with the unique identifier.

At block 706, the label reading station 102 can verify the status of the medication using the data associated with the first unique identifier. Although reference is made to the label reading station 102 verifying the status, it will be understood that in some embodiments, the label reading station 102 receives a status from the information processing system 108 based on an analysis conducted by the information processing system 108, and in certain embodiments, the label reading station 102 analyzes the data to determine the status. In some embodiments, to verify the medication status, the label reading station 102 can determine whether the medication is part of a recall and/or has expired.

To determine whether the medication is part of a recall, the label reading station 102 can cross-reference the lot numbers associated with the first unique identifier (including lot numbers associated with the unique identifiers of all parent medications or parent medicinal containers) with lot numbers that have been recalled. In some embodiments, to verify whether a medication has been recalled, the information processing system 108 can consider only those lot numbers that were created at the same time as or prior to the creation of the database entry corresponding to the first unique identifier. For example, in some instances, a child medication is created or a medication is added to a child medicinal container and then something happens to the medication remaining in the parent medicinal container, or parent medication, such that the parent medication is to subject to a recall or is to be discarded. However, in some embodiments, the recall is only applied to the medication remaining in the parent medicinal container and does not apply to the child medication that was already in the child medicinal container.

To verify the expiration of the medication, the label reading station 102 can determine whether the current date and time is past an expiration date and time of the medication. As part of the expiration verification, the label reading station 102 can identify multiple expirations and use the earliest expiration to determine whether the medication is expired. For example, some medicinal containers may include multiple medications. Each medication may have one or more expirations, the combination of the medications may create a different expiration, and one or more rules may apply to the medications or combination thereof.

For example, some medications have an expiration based on refrigeration and a different expiration when not refrigerated. Similarly, once a seal of a medicinal container is broken, the expiration for a medication, such as a multi-dose medication, may change. For example, while sealed, a medication may have a one year shelf life, but once the seal is broken or punctured, the expiration may change to 60 days from the time the seal was broken or punctured. The broken seal expiration may vary depending on the medication.

In some cases, when a medication is moved to a syringe, the expiration of the medication in the syringe is different than the expiration of the medication in a vial. For example, a medical care facility may have a rule that all syringes expire within 12 hours of being drawn. In certain embodiments, the location of where the syringe is drawn can affect the expiration. For example, a medical care facility may have a rule that syringes drawn in a patient administration environment expire in 24 hours or less, while syringes drawn in a clean room expire in 7 days. Furthermore, in some embodiments, combining two medications can result in a different expiration. As such, in embodiments where multiple expirations are provided, the label reading station 102 can compare the current date and time with the earliest expiration to determine whether the medication is expired. In certain embodiments, only the earliest expiration is provided in conjunction with the unique identifier, and is used to determine whether the medication is expired.

In some embodiments, as part of verifying the status of the medication, the label reading station 102 can determine whether the medical provider has appropriate rights or permissions to handle the medication. For example, some medications can only be handled by certain personnel at a medical care facility. Accordingly, the label reading station 102 can query whether the medical provider that is attempting to handle the medication has the appropriate permissions.

In some embodiments, if the medication cannot be verified, the label reading station 102 can display a warning or disallow the use of the medication. For example, the label reading station 102 can display a warning that the medication is expired or recalled. In addition, when two medications are being combined and the information processing system 108 can, as part of the verification, determine whether the combination would have any adverse reactions. If the information processing system 108 determines that the combination of the two medications would cause an adverse reaction, the label reading station 102 can display a warning or disallow the printing of a label for the combination, etc.

At block 708, the label reading station 102 generates a second expiration date for the medication. The label reading station 102 can generate the second expiration date in a variety of ways. For example in some embodiments the label reading station 102 can use the same expiration date as the parent medication or parent medicinal container. In certain embodiments, the label reading station 102 can generate the second expiration date based on one or more rules associated with the parent medication. For example, once Propofol has been removed from a vial and placed into a syringe, its shelf life decreases to six hours. In such instances, the label reading station 102 can calculate the second expiration date based on the rules of the Propofol, or other applicable rules of the parent medication(s) or medical care facility, as described above.

In embodiments in which multiple parent medications are combined to form the child medication, the label reading station 102 can generate the second expiration date by reviewing the expiration dates of all parent medications that will be used to form the child medication, as well as any rules associated with the parent medications or medical care facility. As mentioned previously, medications and combinations of medications can have various expirations. The label reading station 102 can determine the second expiration date as the earliest expiration date of all of the expiration dates of the parent medications, as well as the expiration date based on any rules associated with the parent medications.

At block 710, the label reading station 102 associates the first RFID tag with a medical care provider. To associate the first RFID tag with the medical care provider, the label reading station 102 can identify the medical care provider that has logged into or scanned their badge prior to scanning the first RFID tag. The label reading station 102 can then associate the first unique identifier of the first RFID tag with a unique identifier of the medical care provider in the data storage device 114 of the information processing system 108. As part of the association, an entry can be added to the information associated with the unique identifier of the RFID tag indicating that the medical care provider has accessed, taken control of, is in possession of, and/or has used the medicinal container associated with the first unique identifier.

At block 712, the label reading station 102 can print medication data on a second label having a second RFID tag. The medication data can include the name of the medication, the expiration of the medication, the concentration of the medication, and/or the total volume of the medication in the second medicinal container. In addition to the medication data, the label reading station 102 can print information regarding the transfer of the medication, including the date and time of the transfer, and the identification of the user that caused the printing to occur.

In some embodiments, the label reading station 102 can print the medication and other data onto the labels described previously with respect to FIGS. 2A and 2B. Furthermore, in some embodiments the second RFID tag can include a second unique identifier that uniquely identifies the RFID tag from all other RFID tags included in the information processing system 108.

At block 714 the label reading station 102 queries the second RFID tag. As described previously with respect to block 702, the label reading station 102 can query the second RFID tag using electromagnetic waves. However, it will be understood that a variety of technologies can be used to query the machine-readable data contained on the second label. In some embodiments, the label reading station 102 can query the second RFID tag during printing of the medication data on to the second label. In certain embodiments the label reading station 102 can query a second RFID tag after printing the medication data onto the second label. In such embodiments, following the printing of the medication data on the second label, a user can tap or move the label onto or in close proximity to, the label reading station 102.

At block 716, the label reading station 102 receives the second unique identifier from the second RFID tag. As mentioned previously, this second unique identifier can be associated with, or used to generate, a new database entry for the data for the child medication or child medicinal container. The database entry can include information similar to the database entry described previously.

At block 718, the label reading station 102 associates the second medicinal container with the medical care provider. For example, the label reading station 102 can associate the second unique identifier with the medical care provider indicating that the medical care provider created, is in possession of, or in some other way used the child medication or child medicinal container associated with the second label. In this way, the information processing system 108 can track the chain of custody of the child medication and/or child medicinal container and provide audit information regarding its location and use.

At block 720, the label reading station 102 can associate the child medication or child medicinal container (using the second unique identifier) with a medical patient. For example, similar to the manner in which the label reading station 102 associates the child medication or child medicinal container with the medical care provider, the label reading station 102 can associate the child medication or child medicinal container with the medical patient. For example, the second unique identifier can be associated with the medical patient indicating that the child medication is to be used for the medical patient.

At block 722, the label reading station 102 determines that the pharmaceutical item storage unit does not store a threshold quantity of the medication. In some embodiments, the label reading station 102 can store a complete inventory of the pharmaceutical item storage unit, such that each time a medicinal container is removed from the pharmaceutical item storage unit, the label reading station 102 can decrement the total number of medicinal containers containing the particular medication. The label reading station 102 can then compare the updated quantity of medicinal containers including a particular medication with a threshold quantity of medicinal containers containing the medication. Upon determining that the quantity of medicinal containers containing the medication does not satisfy the threshold quantity, the label reading station 102 can generate a restocking notification, as illustrated at block 724.

In some embodiments, the label reading station 102 may not store or know the inventory of the medication stored in the pharmaceutical item storage unit. As such, the label reading station 102 can implement a one out one in inventory policy such that each time a particular medication is removed from the pharmaceutical item storage unit, the label reading station 102 can generate a restocking notification to replace the medication that has been removed.

In some embodiments, the label reading station 102 can use one or more templates to determine whether or not the pharmaceutical item storage unit stores a threshold quantity of a medication. The templates can indicate one or more substitute medications and/or substitute quantities that may be used in case a particular medication does not satisfy the threshold quantity. For example, one or more rules may indicate that Advil may be used in place of Tylenol. Accordingly, if a medicinal container including Advil is removed from the pharmaceutical item storage unit, and the total number of Advil in the pharmaceutical item storage unit does not satisfy the threshold quantity of Advil, the label reading station 102 can determine whether or not the number of Tylenol in the pharmaceutical item storage unit satisfies the threshold quantity of Advil. Based upon a determination that the quantity of Tylenol in the pharmaceutical item storage unit satisfies the threshold quantity of Advil, the label reading station 102 can determine that the pharmaceutical item storage unit stores a threshold quantity of Advil. However, in embodiments in which the label reading station 102 determines that the pharmaceutical item storage unit does not store a threshold quantity of Advil (or Tylenol), the label reading station 102 can generate the restocking notification, as illustrated at block 724. The restocking notification can include an email notification, text message, voicemail, page, or other visual and/or audible indication, etc. to enable a user to identify the location of the pharmaceutical item storage unit and medication that is to be replaced.

It will be understood that fewer, more, or different blocks can be used as part of routine 700. For example, the routine 700 can omit block 720 such that the second medicinal container is not associated with a particular medical patient. Such an association can be reserved for a different time, such as when the second label is read by a label reading station 102 that is in close proximity to the patient (for example, when the label reading station 102 is located in an operating room or in the patient's room).

Similarly, in some embodiments the routine 700 can omit blocks 714 and 716. In certain embodiments, the label reading station 102 can determine the second unique identifier of the second RFID tag as it is printing the medication data onto the second label. For example, in some embodiments the label reading station 102 can include a printer that can print RFID tags. In such embodiments, as the label reading station 102 is printing the medication data onto the second label, it can also print the RFID tag. Accordingly, it can determine and/or know the second unique identifier as it is being printed and does not query the RFID tag to receive the second unique identifier.

In some embodiments, the routine 700 can be used when multiple medications are being combined into a child medicinal container or multiple parent medications are used to create a child medication. In such embodiments, the routine 700 can include additional blocks for querying multiple RFID tags associated with the parent medications that are to be combined and receiving the unique identifiers for each parent medication. In such embodiments, the routine 700 can furthermore verify the status of each parent medication, and generate a second expiration date based on the expiration dates of all of the parent medications. In such embodiments, the routine 700 can print child medication data that includes information regarding all of the parent medications that have been used to form the child medication.

Furthermore, routine 700 can include one or more blocks for tracking the inventory of a medical care provider, tracking administration of a medication to a patient, displaying information regarding patients associated with a particular medical care provider, and/or tracking waste, as described in greater detail above with reference to FIGS. 4, 5A, 5B, and 5C, and 6. For example, as part of the administration process, the label reading station 102 can receive a unique identifier associated with a medication, verify the status of the medication, associate the medication with a particular patient, determine whether the particular patient is allergic to the medication or will have any adverse effects when combined with other medications that the particular patient has received, identify discrepancies between an initial amount of the medication in a medicinal container and the amount of the medication administered to the patient, calculate an amount of the medication to waste, and/or track the waste of the medication that was not administered to the patient.

Figure 8:
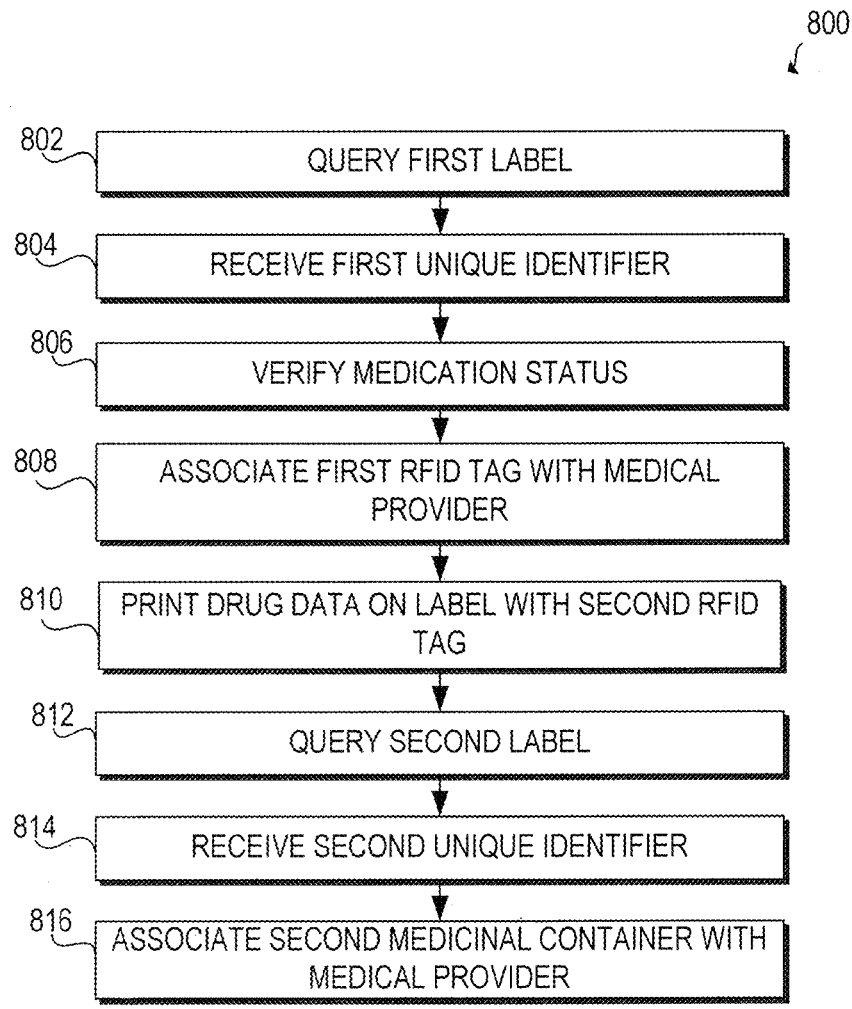
FIG. 8 is a flow diagram illustrating an embodiment for generating a label as part of a transfer of a drug.

FIG. 8 is a flow diagram illustrating an embodiment for generating a label as part of a transfer of a drug. In some embodiments, routine 800 can be used when a medical care provider desires to transfer one or more medications from one or more parent medicinal containers to a child medicinal container or desires to create a child medication from one or more parent medications.

One skilled in the relevant art will appreciate that the elements outlined for routine 800 can be implemented by one or many computing devices/components that are associated with the environment 100, including, but not limited to, the label reading station 102, the information processing system 108, and/or the electronic medical records database 110, or any combination thereof. For simplicity, routine 800 has been associated as being generally performed by the label reading station 102, and thus the following illustrative embodiments should not be construed as limiting.

At block 802, the label reading station 102 queries a first label. The first label can include a first RFID tag, or other machine-readable tag, such as a barcode or QR code. To query the first label, the label reading station 102 can emit an electromagnetic wave that activates an RFID tag of the first label or causes the RFID tag to emit a response, capture an image of a barcode or QR code, and/or use a laser scanner that can read a barcode or QR code.

At block 804, the label reading station 102 receives a first unique identifier from the first label. As mentioned previously, each label can include a unique identifier that uniquely identifies that label from all other labels that are tracked by the information processing system 108. In this way each medicinal container associated with the first label can be uniquely identified. As mentioned previously, the information processing system 108 can include a database entry for each unique identifier.

At block 806, the label reading station 102 can verify the status of the medication using the data associated with the first unique identifier, as described in greater detail above with reference to block 706 of FIG. 7.

At block 808, the label reading station 102 associates the first label with a medical care provider. To associate the first label with the medical care provider, the label reading station 102 can identify the medical care provider that has logged into or scanned their badge prior to querying the first label. The label reading station 102 can then associate the first unique identifier of the first label with a unique identifier of the medical care provider in the data storage device 114 of the information processing system 108. As part of the association, an entry can be added to the information associated with the first unique identifier of the first label indicating that the medical care provider has accessed, taken control of, is in possession of, and/or has used the medicinal container associated with the first unique identifier.

At block 810, the label reading station 102 can print medication data on a second label having a second unique identifier. In some embodiments, the second label can include an RFID tag that includes the second unique identifier. In certain embodiments, the second label can include a barcode or QR code that includes the second unique identifier. The RFID tag, barcode, and/or QR code can be form part of the label prior to printing the medication data or can be printed onto the label with the medication data. In some embodiments, the label reading station 102 can embed some or all of the medication data into the RFID tag, barcode, and/or QR code.

The medication data can include the name of the medication, the expiration of the medication, the concentration of the medication, and/or the total volume of the medication in the medicinal container. In addition to the medication data, the label reading station 102 can print information regarding the transfer of the medication, including the date and time of the transfer, and the identification of the user that caused the printing to occur. In some embodiments, the label reading station 102 can print the medication data and other data onto the labels described previously with respect to FIGS. 2A and 2B.

At block 812, the label reading station 102 queries the second label. As described previously with respect to block 802, the label reading station 102 can query the second label using electromagnetic waves, an image capture, and/or a laser scanner. In some embodiments, the label reading station 102 can query the second label during the printing of the medication data on to the second label. In certain embodiments the label reading station 102 can query the second label after printing the medication data onto the second label. In such embodiments, following the printing of the medication data on the second label, a user can tap or move the label onto or in close proximity to the label reading station 102, scan the label, or capture an image of the label using the label reading station 102.

At block 814, the label reading station 102 receives the second unique identifier from the second label. As mentioned previously, this second unique identifier can be associated with, or used to generate, a new database entry for the data for the child medication or child medicinal container. The database entry can include information similar to the database entry described previously.

At block 816, the label reading station 102 can associate the child medication and/or child medicinal container (using the second unique identifier) with a medical patient. For example, similar to the manner in which the label reading station 102 associates the child medication and/or child medicinal container with the medical care provider, the label reading station 102 can associate the child medication and/or child medicinal container with the medical patient. For example, the second unique identifier can be associated with the medical patient indicating that the contents of the child medicinal container are, or the child medication is, to be used for the medical patient.

It will be understood that fewer, more, or different blocks can be used as part of routine 800. For example, in some embodiments, the routine 800 can include any one or any combination of the blocks described above with respect to routines 700 or 900. In certain embodiments, the routine 800 can omit blocks 812 and 814. In some embodiments, the label reading station 102 can determine the second unique identifier of the second label as it is printing the medication data onto the second label. For example, in some embodiments the label reading station 102 can include a printer that can print RFID tags, barcodes, and/or QR codes. In such embodiments, as the label reading station 102 is printing the medication data onto the second label, it can also print the RFID tag, barcode, and/or QR code. Accordingly, it can determine and/or know the second unique identifier as it is being printed and does not query the RFID tag to receive the second unique identifier.

As described above with respect to routine 700, it will be understood that routine 800 can be used when multiple parent medications are being combined to create a child medication and/or can include one or more blocks for tracking the inventory of a medical care provider, tracking administration of a medication to a patient, displaying information regarding patients associated with a particular medical care provider, and/or tracking waste, as described in greater detail above with reference to FIGS. 4, 5A, 5B, and 5C, and 6.

Figure 9:
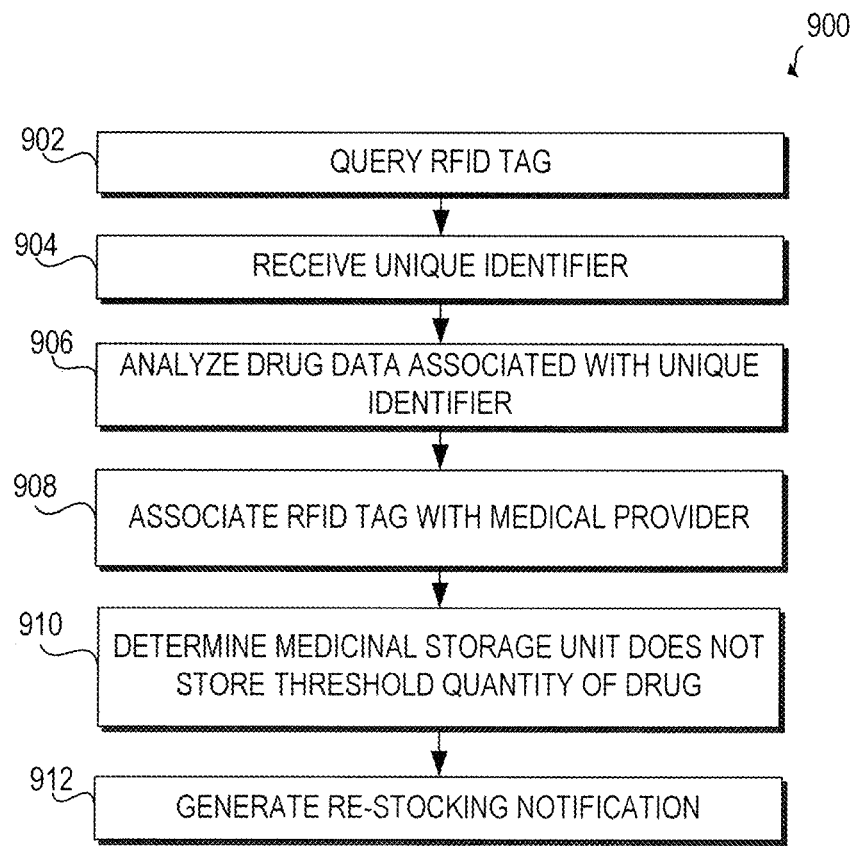
FIG. 9 is a flow diagram illustrating an embodiment for generating a restocking notification.

FIG. 9 is a flow diagram illustrating an embodiment of a routine 900 for generating a restocking notification for a pharmaceutical item storage unit. In some embodiments, routine 900 can be used when a medical care provider removes a medication from the pharmaceutical item storage unit.

One skilled in the relevant art will appreciate that the elements outlined for routine 900 can be implemented by one or many computing devices/components that are associated with the environment 100, including, but not limited to, the label reading station 102, the information processing system 108, and/or the electronic medical records database 110, or any combination thereof. For simplicity, routine 900 has been associated as being generally performed by the label reading station 102, and thus the following illustrative embodiments should not be construed as limiting.

At block 902, the label reading station 102 queries a label. The label can include a RFID tag, or other machine-readable tag, such as a barcode or QR code. To query the label, the label reading station 102 can emit an electromagnetic wave that activates an RFID tag of the label or causes the RFID tag to emit a response, capture an image of a barcode or QR code, and/or use a laser scanner that can read a barcode or QR code.

At block 904, the label reading station 102 receives a unique identifier from the label. As mentioned previously, each label can include a unique identifier that uniquely identifies that label from all other labels that are tracked by the information processing system 108. In this way each medicinal container associated with the label can be uniquely identified. As mentioned previously, the information processing system 108 can include a database entry for each unique identifier.

At block 906, the label reading station 102 can verify the status of the medication using the data associated with the unique identifier, as described in greater detail above with reference to block 706 of FIG. 7.

At block 908, the label reading station 102 associates the label with a medical care provider. To associate the label with the medical care provider, the label reading station 102 can identify the medical care provider that has logged into or scanned their badge prior to querying the label. The label reading station 102 can then associate the unique identifier of the label with a unique identifier of the medical care provider in the data storage device 114 of the information processing system 108. As part of the association, an entry can be added to the information associated with the unique identifier of the label indicating that the medical care provider has accessed, taken control of, is in possession of, and/or has used the medicinal container associated with the unique identifier.

At block 910, the label reading station 102 determines that the pharmaceutical item storage unit does not store a threshold quantity of the medication, and at block 912 the label reading station 102 generates a restocking notification, as described in greater detail above with reference to blocks 722 and 724 of FIG. 7.

It will be understood that few or more or different blocks can be used as part of routine 900. For example, in some embodiments, the routine 900 can include any one or any combination of the blocks described above with respect to routines 700 and/or 800. Furthermore, as described above with respect to routines 700 and 800, it will be understood that routine 900 can include one or more blocks for tracking the inventory of a medical care provider, tracking administration of a medication to a patient, displaying information regarding patients associated with a particular medical care provider, and/or tracking waste, as described in greater detail above with reference to FIGS. 4, 5A, 5B, and 5C, and 6.

Additional Embodiments

It will be understood that the methods and systems described herein can be used in other applications. For example, the process of determining the second expiration date can be used in conjunction with the systems and methods described in U.S. patent application Ser. Nos. 14/472,410, and 13/554,342, incorporated herein by reference. For example, when a medication having a multiple expiration dates or a variable expiration date (for example, a refrigerated/non-refrigerated expiration date, a sealed/broken seal expiration date, and/or a vial/syringe expiration date, etc.), such as a multi-dose medication, is included in a pharmacy kit, the information processing system 108 can verify the medication based on the earliest expiration date or active expiration date. In addition, when an event (for example, breaking the seal, etc.) occurs that alters the expiration date of the medication, the information processing system 108 can update the medication data in the data storage device 114 or in the RFID tag with the new expiration date.

Terminology

Conditional language, such as, among others, "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number respectively. The word "or" in reference to a list of two or more items, covers all of the following interpretations of the word: any one of the items in the list, all of the items in the list, and any combination of the items in the list. Likewise the term "and/or" in reference to a list of two or more items, covers all of the following interpretations of the word: any one of the items in the list, all of the items in the list, and any combination of the items in the list.

Depending on the embodiment, certain operations, acts, events, or functions of any of the algorithms described herein can be performed in a different sequence, can be added, merged, or left out altogether (e.g., not all are necessary for the practice of the algorithms). Moreover, in certain embodiments, operations, acts, functions, or events can be performed concurrently, e.g., through multi-threaded processing, interrupt processing, or multiple processors or processor cores or on other parallel architectures, rather than sequentially.

Systems and modules described herein may comprise software, firmware, hardware, or any combination(s) of software, firmware, or hardware suitable for the purposes described herein. Software and other modules may reside and execute on servers, workstations, personal computers, computerized tablets, PDAs, and other computing devices suitable for the purposes described herein. Software and other modules may be accessible via local memory, via a network, via a browser, or via other means suitable for the purposes described herein. Data structures described herein may comprise computer files, variables, programming arrays, programming structures, or any electronic information storage schemes or methods, or any combinations thereof, suitable for the purposes described herein. User interface elements described herein may comprise elements from graphical user interfaces, interactive voice response, command line interfaces, and other suitable interfaces.

Further, the processing of the various components of the illustrated systems can be distributed across multiple machines, networks, and other computing resources. In addition, two or more components of a system can be combined into fewer components. Various components of the illustrated systems can be implemented in one or more virtual machines, rather than in dedicated computer hardware systems and/or computing devices. Likewise, the data storage devices shown can represent physical and/or logical data storage, including, for example, storage area networks or other distributed storage systems. Moreover, in some embodiments the connections between the components shown represent possible paths of data flow, rather than actual connections between hardware. While some examples of possible connections are shown, any of the subset of the components shown can communicate with any other subset of components in various implementations.

Embodiments are also described above with reference to flow chart illustrations and/or block diagrams of methods, apparatus (systems) and computer program products. Each block of the flow chart illustrations and/or block diagrams, and combinations of blocks in the flow chart illustrations and/or block diagrams, may be implemented by computer program instructions. Such instructions may be provided to a processor of a general purpose computer, special purpose computer, specially-equipped computer (e.g., comprising a high-performance database server, a graphics subsystem, etc.) or other programmable data processing apparatus to produce a machine, such that the instructions, which execute via the processor(s) of the computer or other programmable data processing apparatus, create means for implementing the acts specified in the flow chart and/or block diagram block or blocks.

These computer program instructions may also be stored in a non-transitory computer-readable memory that can direct a computer or other programmable data processing apparatus to operate in a particular manner, such that the instructions stored in the computer-readable memory produce an article of manufacture including instruction means which implement the acts specified in the flow chart and/or block diagram block or blocks. The computer program instructions may also be loaded onto a computing device or other programmable data processing apparatus to cause a series of operations to be performed on the computing device or other programmable apparatus to produce a computer implemented process such that the instructions which execute on the computer or other programmable apparatus provide steps for implementing the acts specified in the flow chart and/or block diagram block or blocks.

Any patents and applications and other references noted above, including any that may be listed in accompanying filing papers, are incorporated herein by reference. Aspects of the invention can be modified, if necessary, to employ the systems, functions, and concepts of the various references described above to provide yet further implementations of the invention.

These and other changes can be made to the invention in light of the above Detailed Description. While the above description describes certain examples of the invention, and describes the best mode contemplated, no matter how detailed the above appears in text, the invention can be practiced in many ways. Details of the system may vary considerably in its specific implementation, while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific examples disclosed in the specification, unless the above Detailed Description section explicitly defines such terms. Accordingly, the actual scope of the invention encompasses not only the disclosed examples, but also all equivalent ways of practicing or implementing the invention under the claims.

To reduce the number of claims, certain aspects of the invention are presented below in certain claim forms, but the applicant contemplates the various aspects of the invention in any number of claim forms. Any claims intended to be treated under 35 U.S.C. § 112(f) will begin with the words "means for", but use of the term "for" in any other context is not intended to invoke treatment under 35 U.S.C. § 112(f). Accordingly, the applicant reserves the right to pursue additional claims after filing this application, in either this application or in a continuing application.

What is claimed is:

1. A system comprising:
one or more processors configured to:
receive, from a label reading station, a first unique identifier, wherein the first unique identifier corresponds to a first computer-readable code associated with a first medicinal container configured to store a first medication;
receive, from the label reading station, a second unique identifier, wherein the second unique identifier corresponds to a second computer-readable code associated with a second medicinal container configured to store a second medication;
identify first drug data using the first unique identifier and second drug data using the second unique identifier, wherein the first drug data corresponds to the first medication and the second drug data corresponds to the second medication;
communicate, to the label reading station, the first drug data and the second drug data;
receive, from the label reading station, a third unique identifier, wherein the third unique identifier corresponds to a third computer-readable code associated with a third medicinal container configured to store a third medication;
determine a drug expiration date of the third medication using the first drug data and the second drug data, wherein the third medication comprises at least a portion of the first medication and the second medication; and
update drug identifier data to associate the drug expiration date of the third medication with the third unique identifier.

2. The system of claim 1, wherein the one or more processors are further configured to communicate the drug expiration date of the third medication to the label reading station.

3. The system of claim 1, wherein to determine the drug expiration date of the third medication, the one or more processors are configured to:
determine a first expiration date using the first drug data, wherein the first expiration date corresponds to an expiration date of the first medication;
determine a second expiration date using the second drug data, wherein the second expiration date corresponds to an expiration date of the second medication; and
identify the drug expiration date as an earlier of the first expiration date and the second expiration date.

4. The system of claim 1, wherein to determine the drug expiration date, the one or more processors are configured to determine the drug expiration date using a predefined rule set corresponding to a combination of the first medication and the second medication.

5. The system of claim 1, wherein the one or more processors are further configured to update the drug identifier data to reflect an expiration date of at least one of the first medication or the second medication to reflect that a sterile barrier has been pierced.

6. The system of claim 1, wherein the label reading station comprises an RFID reader configured to obtain the first unique identifier from an RFID tag.

7. The system of claim 1, wherein the label reading station comprises a barcode scanner configured to obtain the first unique identifier from a barcode.

8. A method comprising:
receiving, from a label reading station, a first unique identifier, wherein the first unique identifier corresponds to a first computer-readable code associated with a first medicinal container configured to store a first medication;
receiving, from the label reading station, a second unique identifier, wherein the second unique identifier corresponds to a second computer-readable code associated with a second medicinal container configured to store a second medication;
identifying first drug data using the first unique identifier and second drug data using the second unique identifier, wherein the first drug data corresponds to the first medication and the second drug data corresponds to the second medication;
communicating, to the label reading station, the first drug data and the second drug data;
receiving, from the label reading station, a third unique identifier, wherein the third unique identifier corresponds to a third computer-readable code associated with a third medicinal container configured to store a third medication;
determining a drug expiration date of the third medication using the first drug data and the second drug data, wherein the third medication comprises at least a portion of the first medication and the second medication; and
updating drug identifier data to associate the drug expiration date of the third medication with the third unique identifier.

9. The method of claim 8, further comprising communicating the drug expiration date of the third medication to the label reading station.

10. The method of claim 8, wherein determining the drug expiration date of the third medication comprises:

determining a first expiration date using the first drug data, wherein the first expiration date corresponds to an expiration date of the first medication;

determining a second expiration date using the second drug data, wherein the second expiration date corresponds to an expiration date of the second medication; and identifying the drug expiration date as an earlier of the first expiration date and the second expiration date.

11. The method of claim 8, wherein determining the drug expiration date of the third medication comprises determining the drug expiration date using a predefined rule set corresponding to a combination of the first medication and the second medication.

12. The method of claim 8, further comprising updating the drug identifier data to reflect an expiration date of at least one of the first medication or the second medication to reflect that a sterile barrier has been pierced.

13. The method of claim 8, wherein the label reading station comprises an RFID reader configured to obtain the first unique identifier from an RFID tag.

14. The method of claim 8, wherein the label reading station comprises a barcode scanner configured to obtain the first unique identifier from a barcode.

15. A non-transitory computer-readable media, comprising computer-executable instructions that when executed by one or more processing devices, cause the one or more processing devices to:

receive, from a label reading station, a first unique identifier, wherein the first unique identifier corresponds to a first computer-readable code associated with a first medicinal container configured to store a first medication;

receive, from the label reading station, a second unique identifier, wherein the second unique identifier corresponds to a second computer-readable code associated with a second medicinal container configured to store a second medication;

identify first drug data using the first unique identifier and second drug data using the second unique identifier, wherein the first drug data corresponds to the first medication and the second drug data corresponds to the second medication;

communicate, to the label reading station, the first drug data and the second drug data;

receive, from the label reading station, a third unique identifier, wherein the third unique identifier corresponds to a third computer-readable code associated with a third medicinal container configured to store a third medication;

determine a drug expiration date of the third medication using the first drug data and the second drug data, wherein the third medication comprises at least a portion of the first medication and the second medication; and update drug identifier data to associate the drug expiration date of the third medication with the third unique identifier.

16. The non-transitory computer-readable media of claim 15, wherein the computer-executable instructions further cause the one or more processing devices to communicate the drug expiration date of the third medication to the label reading station.

17. The non-transitory computer-readable media of claim 15, wherein to determine the drug expiration date of the third medication, the computer-executable instructions cause the one or more processing devices to:

determine a first expiration date using the first drug data, wherein the first expiration date corresponds to an expiration date of the first medication;

determine a second expiration date using the second drug data, wherein the second expiration date corresponds to an expiration date of the second medication; and identify the drug expiration date as an earlier of the first expiration date and the second expiration date.

18. The non-transitory computer-readable media of claim 15, wherein to determine the drug expiration date of the third medication, the computer-executable instructions cause the one or more processing devices to determine the drug expiration date using a predefined rule set corresponding to a combination of the first medication and the second medication.

19. The non-transitory computer-readable media of claim 15, wherein the computer-executable instructions further cause the one or more processing devices to update the drug identifier data to reflect an expiration date of at least one of the first medication or the second medication to reflect that a sterile barrier has been pierced.

20. The non-transitory computer-readable media of claim 15, wherein the label reading station comprises at least one of:

an RFID reader configured to obtain the first unique identifier from an RFID tag; and a barcode scanner configured to obtain the first unique identifier from a barcode.

* * * * *